United States Patent [19]

Tsang et al.

[11] Patent Number: 5,091,377
[45] Date of Patent: Feb. 25, 1992

[54] TRISUBSTITUTED SILYLALKYL 1,2,4-TRIAZOLE AND IMIDAZOLE PHENYL BORANE DERIVATIVES

[75] Inventors: Tsze H. Tsang, El Cerrito, Calif.; Vincent J. Spadafora, Morrisville, Pa.

[73] Assignee: Chevron Research and Technology Company, San Francisco, Calif.

[21] Appl. No.: 628,806

[22] Filed: Dec. 14, 1990

[51] Int. Cl.$^5$ .......................... A01N 55/08; C07F 7/02
[52] U.S. Cl. ........................................ 514/63; 548/110
[58] Field of Search ........................... 514/63; 548/110

[56] References Cited

U.S. PATENT DOCUMENTS

| | | | |
|---|---|---|---|
| 3,062,708 | 11/1962 | Updegraff | 167/30 |
| 3,211,679 | 10/1965 | Updegraff | 260/19 |
| 3,686,398 | 8/1972 | Kohn et al. | 424/185 |
| 3,692,798 | 9/1972 | Barcza | 260/309 |
| 3,696,103 | 10/1972 | Cometti | 260/268 |
| 4,510,136 | 4/1985 | Moberg | 514/63 |
| 4,613,373 | 9/1986 | Umeno | 106/183 |
| 4,804,653 | 2/1989 | Strunk et al. | 514/63 |
| 4,983,589 | 1/1991 | Tsang et al. | 514/64 |
| 4,983,590 | 1/1991 | Tsang et al. | 514/64 |

FOREIGN PATENT DOCUMENTS 62-277307  5/1986  Japan .

OTHER PUBLICATIONS

Derwent Abstract 5188957.
Compte Rendus Hebdomadaires des Seances de l'Academie des Sciences, p. 319, vol. 254 (1962).

*Primary Examiner*—Patricia L. Morris
*Attorney, Agent, or Firm*—R. C. Gaffney; L. S. Squires

[57] ABSTRACT

Trisubstituted silyalkyl 1,2,4-triazole and imidazole phenyl borane compounds having the formula:

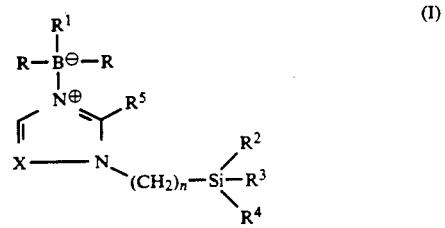

wherein n, X, R, $R^1$, $R^2$, $R^3$, $R^4$, and $R^5$ are defined in the description, and processes and intermediates for the preparation thereof are disclosed.

The compounds of Formula I are especially useful as agricultural fungicides.

26 Claims, No Drawings

TRISUBSTITUTED SILYLALKYL 1,2,4-TRIAZOLE AND IMIDAZOLE PHENYL BORANE DERIVATIVES

BACKGROUND OF THE INVENTION

This invention relates to certain arylsilylalkylimidazoles or triazole triaryl- and diaryl-aliphenylboranes, and derivatives thereof. In a further aspect, the invention relates to the use of such complexes as agricultural fungicides.

A large amount of crop loss and plant damage is incurred each year due to plant diseases caused by four classes of fungi Ascomycetes, causing a large number of leaf spots, blights, soil-bourn and post-harvest diseases; Deuteromycetes, also causing a large number of leaf spots, blights, soil-bourn and post-harvest diseases; Basidiomycetes, causing rust, smuts, bunts and soil bornediseases; and Phycomycetes, causing downy mildews, leaf blights and soil-bourn diseases.

Leaf spot and blight diseases, such as those induced by species of Leptosphaeria, Mycosphaerella, Alternaria, and Helminthosporium cause damage to many crops such as maize, wheat, banana, and solanaceous crops and are difficult to control.

Various species of the genus Botrytis are responsible for diseases causing large losses in numerous vegetable, ornamental and vine crops. Present fungicides such as benzimidazoles and dicarboximides cannot adequately control these diseases due to the development of resistance by the pathogen.

The late blights and downy mildew plant diseases produced, for example, by Phytophthora and Plasmopara are very destructive to grape and solanaceous crops, e.g., potato, tomato. These diseases are also difficult to control due to the development of resistance to the leading systemic fungicides used to control these diseases.

Thus, it would be desirable to develop new fungicides which are effective to control plant diseases and especially in the case of late blights, mildew and Botrytis-produced diseases which are not subject to cross-resistance of the pathogen and which do not cause significant injury to the plants (i.e., are relatively non-phytotoxic).

Flusilazole, i.e., 1-([bis(4-fluorophenyl) methylsilyl]-methyl)-1h-1,2,4-triazole is a commercial fungicide generally described as useful to control ascomycete, basidiomycete and deuteromycete fungi in cereals, fruits and vegetables by the farm chemicals handbook (1989) p. c-135.

U.S. Pat. No. 3,062,708 generally teaches that amine complexes of triphenylborane with certain lewis bases have anti-fungal activity. The patent shows in vitro activity with respect to triphenylborane-imidazole and illustrates in vitro activity against tomato early blight, bean rust, late blight and seed rot (pythium ultimum) with respect to certain triphenylborane amines including complexes with piperidine, pyridine and 4-ethyl-pyridine.

U.S. Pat. No. 3,211,679 teaches that triarylborane amine complexes with pyridine or a variety of substituted pyridines are useful as toxicants for anti-fouling paint and that such paints impart residual toxicity to marine borers in wood structures.

U.S. Pat. No. 3,686,398 teaches that certain 10,9-boroxarophenanthrenes are useful to control fungi and exhibit preventative control of bean rust and celery late blight.

U.S. Pat. No. 3,692,798 describes a genus of substituted silylmethyl imidazoles and teaches that their compounds are useful as anti-microbials.

U.S. Pat. No. 3,696,103 teaches that certain di(substituted and unsubstituted phenyl)azaborolidines exhibit fungicidal, insecticidal, acaricidal and herbicidal activity. The fungicidal activity is described as polyvalent and is shown against bean anthracnose (*Collectrotrichum lindemythianum*), tomato mildew (late blight) (*Phytophthora infestans*), tobacco mildew (blue mold) (*Peronospora tabaci*), cucumber (powdery) mildew (*Erysiphe cichoracearum*) and wheat rust (*Puccinia glumarum*) at quantities of between 10 and 200 g of active substance per hectoliter of liquid diluent such as water.

U.S. Pat. No. 4,510,136 describes a genus of (optionally substituted diphenyl)alkyl(optionally substituted 1H-1,2,4-triazole-1-ylmethyl)silane fungicides.

U.S. Pat. No. 4,613,373 teaches that certain tetra-(substituted and unsubstituted phenyl) boranes complexed with a heterocyclic amine are useful as anti-fouling, antiseptic, and anti-fungal agents in many industrial applications. In vitro inhibiting activity of certain of patentee's, compounds against certain fungi are shown in Table 4 of the patent.

Based on the Derwent Abstract, Japanese Patent Application Publication 62-277307 describes complexes of tri(substituted phenyl)borane with amines and nitrogen containing heterocycles as useful as insecticides, miticides and nematocides. Based on Derwent Abstract 5188957, Japanese Patent Application publication JP 1056684 published Mar. 3, 1989 discloses certain tetraphenylboron-onium complexes useful as agricultural and industrial fungicides.

SUMMARY OF THE INVENTION

The present invention provides compounds having fungicidal activity against certain plant diseases and which exhibit no crop phytotoxicity or low levels of phytotoxicity which are within acceptable limits. Certain of the compounds exhibit protective or preventative activity against a broad spectrum of Botrytis diseases, mildews and blights and leaf spot and leaf blights induced by Septoria, and are not affected by cross-resistance of the pathogen to other fungicides. Certain of the compounds further exhibit eradicant activity with respect to certain fungal diseases, although generally more effective as preventative fungicides. The present invention is based in part on the surprising discovery that by complexing certain triazolesilanes and imidazolesilanes with certain organoboranes that the magnitude of fungicidal activity and/or the spectrum of fungicidal activity is greatly improved.

The present invention provides organoborane 1,2,4-triazole and imidazole complexes having the following formula:

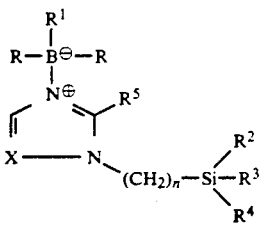
(I)

wherein:
 n is 1 or 2;
 R is styryl or the group

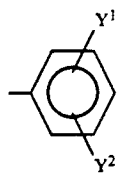

wherein $Y^1$ is hydrogen; lower alkyl having 1 through 6 carbon atoms; fluoro; chloro; lower alkoxy having 1 through 6 carbon atoms, lower alkylthio having 1 through 6 carbon atoms; and $Y^2$ is hydrogen; lower alkyl having 1 through 6 carbon atoms; lower alkythio having 1 through 6 carbon atoms; or the group

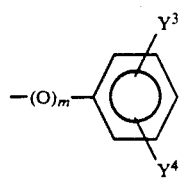

wherein m is 0 or 1 and $Y^3$ and $Y^4$ are independently selected from the group of substitutes defined for $Y^1$;
 $R^2$ and $R^3$ are independently selected from the group

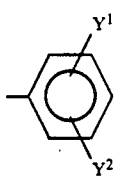

wherein $Y^1$ and $Y^2$ are as defined with respect to R;
 $R^1$ and $R^4$ are independently selected from the group of alkyl having 1 through 4 carbon atoms; cycloalkyl having 3 through 6 carbon atoms; lower alkenyl having 2 through 6 carbon atoms; haloalkenyl having 3 through 6 carbon atoms and 1 through 4 halo atoms independently selected from the group of fluoro, chloro, and bromo; or the group

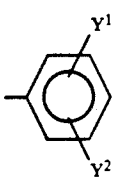

wherein $Y^1$ and $Y^2$ are defined with respect to R;
 X is N or CH; and $R^5$ is hydrogen or alkyl having 1 through 4 carbon atoms when X is CH and hydrogen when X is N.

In those cases where the complex of Formula I has an asymmetric carbon atom, the compounds can exist as optical isomers. In some instances the compounds also exist as geometric isomers, for example, where R is an alkenyl group having a cis-trans double bond. In addition, the compounds can exist as chelation, or linkage isomers, in the case of triazoles (where X=N and $R^5$ is hydrogen), wherein boron is coordinated to the N2 or the N4 nitrogen.

The above formula is intended to encompass the respective individual isomers as well as mixtures thereof and the respective individual isomers as well as mixtures thereof are encompassed within the invention.

In a further aspect, the invention provides a fungicidal composition comprising a compatible carrier and a fungicidally effective amount of the compound(s) of the invention or mixtures thereof.

The invention also provides a method for preventing or controlling fungi, which comprises applying an amount of a compound of Formula I or mixtures thereof to such fungi or its habitat which is effective to prevent or inhibit or arrest the growth of the fungi.

In another aspect the invention provides a method for preventing or controlling fungal plant diseases which comprises applying to the plant an amount of the compound(s) of Formula I or mixtures thereof which is effective to prevent or inhibit the growth of the fungal pathogen producing the disease.

The present invention also provides chemical intermediates and processes for preparing the compounds of Formula I.

The invention will be further described herein below.

FURTHER DESCRIPTION OF THE INVENTION AND THE PREFERRED EMBODIMENTS

The compounds of the present invention can also be represented by the following imidazole and 1,2,4-triazole subgeneric formulas:

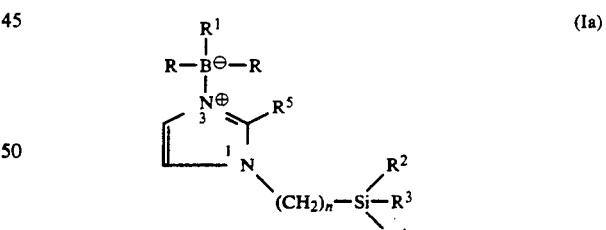
(Ia)

and

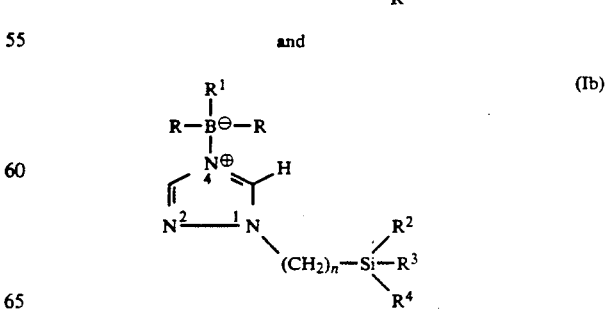
(Ib)

wherein R, $R^1$, $R^2$, $R^3$, $R^4$ and $R^5$ are defined hereinabove.

Illustrations of typical compounds of Formula I can be had by reference to Examples 2, 3, and 5 set forth hereinbelow.

Based on consideration of magnitudes of fungicidal activity, spectrum of fungicidal activity, plant safety, and/or ease of manufacture, the preferred compounds are those of subgenus (Ib), and especially the species wherein at least one substituent is selected from the group R is phenyl; $R^1$ is methyl or vinyl; $R^2$ is 4-chlorophenyl or 4-fluorophenyl; $R^3$ is methyl; $R^4$ is 4-chlorophenyl or 4-fluorophenyl.

The preferred species of Formula Ia, are also those having at least one substituent selected from the group R is phenyl; $R^1$ is methyl or vinyl; $R^2$ is 4-chlorophenyl or 4 fluorophenyl; $R^3$ is methyl; $R^4$ is 4-chlorophenyl or 4-fluorophenyl and $R^5$ is hydrogen. More preferably, the species of Ia and Ib have two or more preferred substituents and most preferably, all of the substituents are preferred substituents. Also, in terms of manufacturing ease the compounds preferably are substituted with the same substituent at both $R^2$ and $R^4$.

Definitions

As used herein the following terms have the following meanings unless expressly stated to the contrary:

The term "alkyl" refers to both straight- and branched-chain alkyl groups. The term "lower alkyl" refers to alkyl groups having a total of from 1 through 6 carbon atoms, preferably 1 through 4 carbon atoms and includes primary, secondary and tertiary alkyl groups. Typical lower alkyls include, for example, methyl, ethyl, n-propyl, isopropyl, n-butyl, t-butyl, pentyl, hexyl and the like.

The term "lower alkenyl" refers to alkenyl groups having 2 through 6, preferably 2 through 4, carbon atoms and includes, for example, vinyl, 1-propenyl, 2-propenyl, 1-methylvinyl, 1-butenyl, 2-methylprop-1-enyl and the like.

The term "lower alkoxy" refers to the group —OR' wherein R' is lower alkyl.

The term "lower alkylthio" refers to the group R'S≧ wherein R' is a straight chain or branched chain alkyl group having 1 through 3 carbon atoms.

The term "halo" refers to the group of fluoro, chloro, bromo and iodo unless expressly defined as referring only to fluoro, chloro and bromo.

The term "aralkyl" refers to the group

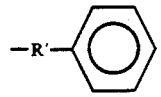

wherein R' is lower alkyl having 1 through 4 carbon atoms and preferably has 1 or 2 carbon atoms.

The term "lower haloalkyl" refers to haloalkyl compounds having 1 through 4 carbon atoms and 1 through 3 halo atoms independently selected from the group of fluoro, chloro, and bromo. Preferably the lower haloalkyl group has 1 or 2 carbon atoms.

The term "room temperature" or "ambient temperature" refers to about 20°–25° C.

In naming compounds the following examples illustrate the nomenclature which will be used:

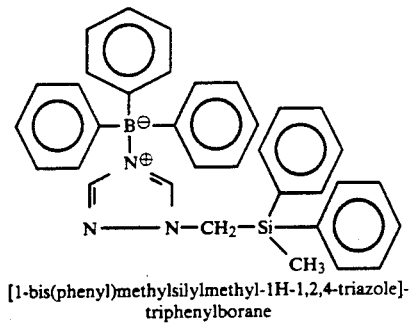

[1-bis(phenyl)methylsilylmethyl-1H-1,2,4-triazole]-triphenylborane

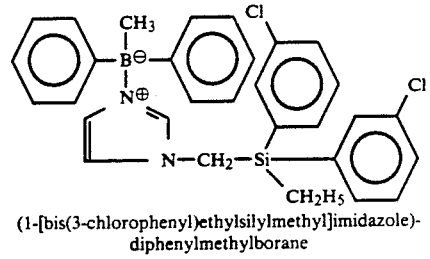

(1-[bis(3-chlorophenyl)ethylsilylmethyl]imidazole)-diphenylmethylborane

Synthesis

The compounds of Formula I wherein $R^1$ is phenyl or a substituted phenyl can be prepared via the following schematically represented process:

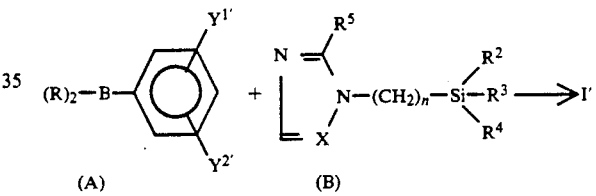

wherein $R^2$, $R^3$, $R^4$, $R^5$, X, $Y^1$ and $Y^2$ are as defined hereinabove and $Y^{1'}$ and $Y^{2'}$ as selected from the same substituents as defined for $Y^1$ and $Y^2$ respectively and I' corresponds to Formula I wherein $R^1$ is phenyl or a mono- or a di-substituted phenyl.

This process can be effected by contacting Compound (A) with Compound (B) under reactive conditions, preferably in an inert organic solvent under substantially anhydrous conditions. Typically, this step is conducted at temperatures in the range of about from 10° C. to 40° C. preferably 20° C. to 30° C. for about from 8 to 15 hours, preferably about from 10 to 12 hours, using about from 1.5 to 1.0, preferably 1.0 to 1.0 moles, of Compound (B) per mole of Compound (A).

Suitable organic solvents which can be used include, for example, tetrahydrofuran, alkyl ethers, (e.g. ethyl ether), hexane, and the like, and compatible mixtures thereof. Best results are obtained using tetrahydrofuran, ethyl ether, or glyme as the solvent.

The starting materials of Formulas (A) and (B) are generally known materials and can be prepared by known procedures or obvious modifications thereof (e.g. substitution of appropriately substituted reactants, use of appropriate solvents, etc.). For Formula (A), where R=phenyl and both $Y^{1'}$ and $Y^{2'}$ =H, the compound is commercially available. Procedures for preparing compounds of Formula (B) are described in U.S. Pat. Nos. 3,692,798 and 4,510,136, hereby incorporated by reference in their entirety. In the case where $R^5$ is other than hydrogen the appropriate $R^5$ substitute imidazole is used.

Substituted imidazoles can be prepared according to known procedures such as, for example, described in M. R. Grimmett, *Advances in Heterocyclic Chem.* 12, 103 (1970), Ibid. 27, 241 (1980) and in many instances are commercially available. The 2-substituted imidazoles are generally commercially available or can be prepared by the classical Radszizewski reaction with glyoxal, suitable aldehydes, and ammonia in a single step. Di- or tri-substituted imidazoles can be prepared similarly. The di- or tri-substituted imidazole can be prepared by lithiating and alkylating of mono-substituted imidazoles as described in B. H. Lipshutz, B. Huff, W. Hazen, Tetrahedron Letter 29, 3411 (1988).

The compounds of Formula I wherein $R^1$ is alkyl, cycloalkyl, alkenyl, or haloalkyl can be prepared by the following schematically represented process:

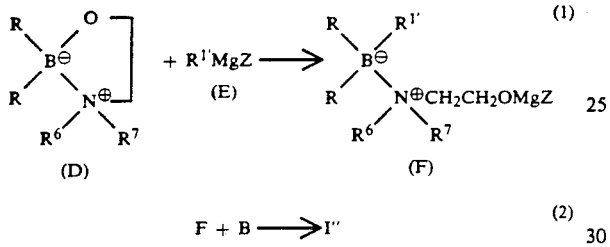

$$F + B \longrightarrow I'' \qquad (2)$$

wherein R is as defined hereinabove; $R^{1'}$ is alkyl, cycloalkyl, alkenyl or haloalkyl, $R^6$ and $R^7$ are independently hydrogen or lower alkyl, preferably hydrogen or methyl, and Z is chloride, bromide or iodide.

Step 1 of this process is a Grignard reaction and typically is effected by contacting Compound (D) with the Grignard Reagent (E) under reactive conditions, preferably in an inert organic solvent under substantially anhydrous conditions. Typically, this step is conducted at temperatures in the range of about from 15° C. to 80° C., preferably 20° C. to 35° C., for about from 2 to 24 hours, preferably about from 2 to 4 hours, using about from 1 to 3.5, preferably 1 to 3 moles of Grignard Reagent (E) per mole of Compound (A).

Suitable organic solvents which can be used include, for example, tetrahydrofuran, alkyl ethers (e.g. ethyl ether), hexane, and the like, and compatible mixtures thereof. Best results are obtained using tetrahydrofuran, ethyl ether or glyme as the solvent.

The second step can be effected by contacting intermediate F, with the desired organosilyl imidazole or triazole (B), preferably in an inert organic solvent, under reactive conditions. The second step can be conveniently conducted in situ without separation of intermediate F from the reaction product mixture of step 1.

Typically, this process is conducted at temperatures in the range of about from 20° C. to 35° C., preferably 20° C. to 25° C., for about from 2 to 24 hours, preferably 10 to 24 hours, using about from 1 to 5, preferably 1 to 3 moles of Compound (B) per mole of Compound (F) or (D), when the reaction is conducted in situ. Typically, about from 1 to 3 moles of base are used per mole of Compound (B).

Suitable inert organic solvents which can be used include, for example, the solvents listed above with respect to Step 1, and compatible mixtures thereof. Since most conveniently, the second step is conducted in situ, the same solvent will generally be used in the second step as used in the first step.

The starting materials of Formulas (D) and (E) are generally known materials and can be prepared by known procedures, or obvious modifications thereof (e.g., substitution of appropriate starting materials). The preparation of starting material (D) is, for example, described in Y. Rasiel and H. K. Zimmerman, Ann. 649, 111 (1961) or by R. L. Lestinger and I. Skoog, J. Am. Chem. Soc. 77, 2491 (1955), and in the case where R, $R^6$ and $R^7$ are hydrogen, is a commercially available material. The starting materials of Formula (E) are Grignard Reagents and can be prepared via standard procedures such as, for example, described in P. E. Pearson, D. Cowan, J. D. Becker, J. Org. Chem. 24, 504 (1959). The starting materials of Formula (D) can also be prepared by hydrolysis and oxidation of the corresponding optionally substituted triphenylborane alkali metal hydroxide adduct.

The compounds of Formula I also generally can be conveniently prepared via the process described by P. Kenny, using an exchange reaction of an imidazole with a diphenyl-alkylboron-ammonia complex:

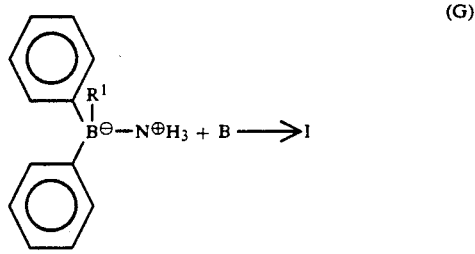

wherein R, $R^1$ and Y are defined hereinabove.

In accordance with this process, Compound (G) is contacted with Compound (B) under reactive conditions, preferably in an inert organic solvent under substantially anhydrous conditions.

Preferably, this process is conducted at temperatures in the range of about from 0° C. to reflux, conveniently about 20° C. to 25° C. for about 1 to 72 hours, using about from 0.1 to 1 mole of Compound (B) per mole of Compound (G). Suitable inert organic solvents which can be used include, for example, halogenated alkanes, for example, chloroform, methylene chloride; lower alkenols, for example, methanol, ethanol; acetone and the like and compatible mixtures thereof. The starting material of Formula (G) can be prepared by known procedures such as, for example, described by D. Giraud, et al. in *Compte Rendus Hebdomadaires des Sciences de l'Academie des Sciences,* p. 319, v. 254 (1962), or by obvious modifications thereof (e.g., use of appropriately substituted reactants and appropriate solvents). Compound (G) can also be conveniently prepared via the reaction of intermediate F with ammonia.

General Process Conditions

In the above-described processes, the products can be recovered from the respective reaction product mixtures by any suitable separation and purification procedure, such as, for example, extraction, trituration, and recrystallization. Suitable separation and purification procedures are, for example, illustrated in the Examples set forth hereinbelow.

Generally, the reactions described above are conducted as liquid phase reactions and hence pressure is generally not significant except as it affects temperature (boiling point) where reactions are conducted at reflux. Therefore, these reactions are generally conducted at pressures of about from 300 to 3,000 mm of mercury and conveniently are conducted at about atmospheric or ambient pressure.

It should also be appreciated that where typical or preferred process conditions (e.g., reaction temperatures, times, mole ratios of reactants, solvents, pressures, etc.) have been given, that other process conditions could also be used unless otherwise stated. Optimum reaction conditions (e.g., temperature, reaction time, mole ratios, solvents, etc.) may vary with the particular reagents or organic solvents used but can be determined by routine optimization procedures.

Where optical isomer mixtures are obtained, the respective optical isomers can be obtained by conventional resolution procedures. Geometric isomers and coordination isomers can be separated by conventional separation procedures which depend upon differences in physical properties between the isomers.

Utility

The compounds of the present invention are effective in controlling fungal plant diseases, including downy mildew, leaf blights, leaf spots, damping-off diseases, Botrytis diseases, and post-harvest diseases. Certain of the compounds further exhibit a broad spectrum of activity. The compounds are generally more effective as preventative fungicides and a number of which are especially effective in preventing grey mold (Botrytis), grape downy mildew, late blights in solanaceous crops, and Septoria leaf spot diseases. For example [1-bis(4-fluorophenyl)methylsilylmethyl-1H-1,2,4-triazols]-triphenylborane and its diphenylvinylborane analog exhibit very good preventative activity against grape downy mildew disease caused by *Plasmopara viticola*.

The compounds are applied to the subject plants in fungicidally effective amounts. When applied as preventative fungicides, the compounds are preferably applied at pre-scheduled times prior to the detection of plant infection or immediately upon the detection of infection. The optimum fungicidally effective amount will, of course, depend on several factors such as the host, the type of fungus, weather conditions, and the particular compound of the invention. Generally, however, the compounds are preferably applied at a rate of about from 0.2 to 2.5 kg per hectare for preventative application, and 1 to 3 kg per hectare for eradicant application. The compounds may also be applied for seed treatments. Generally, the compounds are applied as seed treatments at a rate of about 0.5 to 32 g per 100 kg of seeds. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable solutions, as emulsifiable concentrates, as solutions, or as any of several other known types of formulations, depending on the desired mode of application.

Wettable powders are in the form of finely divided particles which disperse readily in water or other dispersant. These compositions normally contain from about 5% to 80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively course particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art. The percentages by weight of the fungicide may vary according to the manner in which the composition is to be applied and the particular type of formulation, but in general comprise 0.05% to 95% of the toxicant by weight of the fungicidal composition, and depending on whether the composition is intended for direct application or dilution prior to application. The compounds are typically applied at rates in the range of about from 0.1 to 5 kg/hectare, preferably 0.2 to 3 kg/hectare, and typically are applied as foliage sprays.

The fungicidal compositions may be formulated and/or applied with other ingredients, including wetting agents, emulsifiers, adjuvants, stabilizers, etc., as well as other compatible active ingredients such as other fungicides, insecticides, nematocides, bactericides, plant growth regulators, fertilizers, etc.

A further understanding of the invention can be had in the following non-limiting Preparation(s) and Example(s). Wherein, unless expressly stated to the contrary, all temperatures and temperature ranges refer to the Centigrade system and the term "ambient" or "room temperature" refers to about 20°-25° C. The term "percent" or "%" refers to weight percent and the term "mole" or "moles" refers to gram moles. The term "equivalent" refers to a quantity of reagent equal in mole equivalents to the mole equivalent of the preceding or succeeding reactant recited in that example or preparation in terms of finite moles or finite weight or volume.

PREPARATIONS AND EXAMPLES

PREPARATION A

Bis(4-Fluorophenyl)methylsilymethyl Chloride

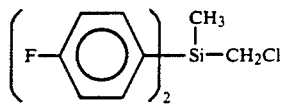

In this preparation 23.5 mmol of (chloromethyl)methylsilyl dichloride is added dropwise over a fifteen minute period to a solution of 58 mmol of 4-fluorophenyl magnesium bromide in tetrahydrofuran at −78° C. The resulting mixture is allowed to warm to room temperature and stirred overnight (about 14–16 hours). The mixture is then quenched by the addition of 100 mL of water and then extracted three times with 50 mL portions of ethyl ether. The extracts are combined, washed with 100 mL saturated aqueous sodium chloride solution (brine) and dried over magnesium sulfate. The ethyl ether is evaporated off affording the title compound as a pale yellow oil.

PREPARATION B

1-[Bis(4-fluorophenyl)methylsilylmethyl]-1,2,4-Triazole

In this preparation 1.0 g of sodium 1,2,4-triazole is added to a solution of 3.1 g of bis(4-fluorophenyl)methylsilylmethyl chloride in 15 mL of dimethylformamide. The mixture is heated at about 80°-90° C. for two hours and then cooled to room temperature. The mixture is then diluted with 60 ml of water and extracted three times with 50 ml portions of ethyl ether. The extracts are combined, washed twice with 80 ml of water, then with 80 ml of aqueous saturated sodium chloride solution and dried over magnesium sulfate. The ethyl ether solvent is evaporated off affording an oil which is then purified by chromatography over silica gel solution with ethyl acetate, hexane, and mixture thereof.

Similarly, by following the same procedure but using a mole equivalent of sodium imidazole in place of sodium 1,2,4-triazole the corresponding imidazole analog can be prepared, i.e., 1-[Bis-(4-fluorophenyl)methylsilylmethyl]imidazole.

PREPARATION C

2-Aminoethyl Diphenylborinate

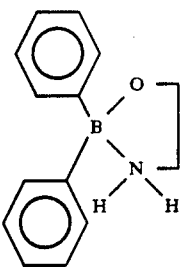

This preparation illustrates the preparation of the title compound via the method of P Denisevich, Jr.

Aqueous 10 wt. % hydrochloric acid is slowly added to 250 g of a solution containing 22.5 g of triphenylborane.sodium hydroxide. The addition of hydrochloric acid is continued until a pH of 1.2. During the addition, cooling is provided to maintain the temperature of the reaction mixture below 30° C. Eighty (80) ml of ethyl ether is added and the mixture stirred overnight (about 10–12 hours) at room temperature during which time a slow steady stream of air is passed through the mixture. Fifty (50) ml of ethyl ether is added to compensate for evaporation losses. The reaction mixture forms a two-phase system. The ethyl ether phase is separated, washed with water and then added to 4.9 g of 2-aminoethanol. The mixture is stirred for one hour at room temperature and then filtered. The recovered solids are washed with water, affording 14.4 g of the title compound m.p. 186°-188° C.

EXAMPLE 1

Diphenylmethylborane-2-Aminoethoxymagnesium Bromide

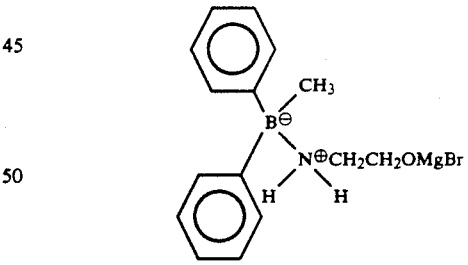

The title compound can be prepared by adding dropwise 0.0064 mole of methyl magnesium bromide in 72 ml of tetrahydrofuran to 30 mL of diethyl ether containing 1.43 g (0.0064 mole) of the title compound of Preparation C under an inert nitrogen atmosphere. The solution is heated at reflux for one hour and then allowed to cool. It is unnecessary to separate the product so formed from the solution, as the final step in the preparation may be carried out in situ, in the same solution in which the intermediate is formed.

In a similar manner, diphenyl vinyl- and diphenylcyclopropylborane-2-aminoethoxymagnesium bromides can be prepared

EXAMPLE 2

1-[Bis(4-fluorophenyl)methylsilylmethyl]Imidazole-Diphenylmethylborane

The title compound can be prepared by adding 2.00 g of 1-[bis(4-fluorophenyl)methylsilylmethyl]imidazole to the intermediate reaction product mixture of Example 1, and stirring the solution overnight. The next day, a 1% solution of HCl and 200 ml of diethyl ether are added. the ether layer is removed and the aqueous layer is extracted twice more with 50-ml portions of diethyl ether. the ether layers are combined and dried over magnesium sulfate. After removal of the diethyl ether, a clean oil results. This oil is dissolved in a minimum amount of ethanol and water is added dropwise slowly to precipitate the product. The process yields approximately 2.1 g of a solid white powder with a melting point of 100°-111° c.

Similarly, by applying the above referenced procedure using the appropriate starting materials, the following compounds can be prepared:

(1-[triphenylsilylmethyl]imidazole)-diphenylmethylborane
(1-[bis(phenyl)methylsilylmethyl]imidazole)-diphenylmethylborane
(1-[bis(phenyl)ethylsilylmethyl]imidazole)-diphenylmethylborane
(1-[bis(phenyl)-n-propylsilylmethyl]imidazole)-diphenylmethylborane
(1-[bis(phenyl)-i-propylsilylmethyl]imidazole)-diphenylmethylborane
(1-[bis(phenyl)-n-butylsilylmethyl]imidazole)-diphenylmethylborane
(1-[bis(phenyl)-i-butylsilylmethyl]imidazole)-diphenylmethylborane
(1-[bis(phenyl)-t-butylsilylmethyl]imidazole)-diphenylmethylborane
(1-[bis(phenyl)cyclopropylsilylmethyl]imidazole)-diphenylmethylborane
(1-[bis(phenyl)cyclobutylsilylmethyl]imidazole)-diphenylmethylborane
(1-[bis(phenyl)cyclopentylsilylmethyl]imidazole)-diphenylmethylborane
(1-[bis(phenyl)cyclohexylsilylmethyl]imidazole)-diphenylmethylborane
(1-[bis(phenyl)vinylsilylmethyl]imidazole)-diphenylmethylborane
(1-[bis(phenyl)-1-propenylsilylmethyl]imidazole)-diphenylmethylborane
(1-[bis(phenyl)-2-propenylsilylmethyl]imidazole)-diphenylmethylborane
(1-[bis(phenyl)-1-methylvinylsilylmethyl]imidazole)-diphenylmethylborane
(1-[bis(phenyl)-1-butenylvinylsilylmethyl]imidazole)-diphenylmethylborane
(1-[bis(phenyl)-1-methylprop-1-enylsilylmethyl]imidazole)-diphenylmethylborane
(1-[bis(phenyl)-2-methylprop-1-enylsilylmethyl]imidazole)-diphenylmethylborane
(1-[bis(phenyl)-1-methylprop-2-enylsilylmethyl]imidazole)-diphenylmethylborane
(1-[bis(phenyl)-2-methylprop-2-enylsilylmethyl]imidazole)-diphenylmethylborane
(1-[bis(phenyl)-2-butenylsilylmethyl]imidazole)-diphenylmethylborane
(1-[bis(phenyl)-3-butenylsilylmethyl]imidazole)-diphenylmethylborane
(1-[bis(phenyl)-1-pentenylsilylmethyl]imidazole)-diphenylmethylborane
(1-[bis(phenyl)-2-pentenylsilylmethyl]imidazole)-diphenylmethylborane
(1-[bis(phenyl)-3-pentenylsilylmethyl]imidazole)-diphenylmethylborane
(1-[bis(phenyl)-4-pentenylsilylmethyl]imidazole)-diphenylmethylborane
(1-[bis(phenyl)-2-methylbut-2-enylsilylmethyl]imidazole)-diphenylmethylborane
(1-[bis(phenyl)-2-methylbut-3-enylsilylmethyl]imidazole)-diphenylmethylborane
(1-[bis(phenyl)-3-methylbut-1-enylsilylmethyl]imidazole)-diphenylmethylborane
(1-[bis(phenyl)-3-methylbut-2-enylsilylmethyl]imidazole)diphenylmethylborane
(1-[bis(phenyl)-3-methylbut-3-enylsilylmethyl]imidazole)-diphenylmethylborane
(1-[bis(phenyl)-1-hexenylsilylmethyl]imidazole)-diphenylmethylborane
(1-[bis(phenyl)-2-hexenylsilylmethyl]imidazole)-diphenylmethylborane
(1-[bis(phenyl)-3-hexenylsilylmethyl]imidazole)-diphenylmethylborane
(1-[bis(phenyl)-4-hexenylsilylmethyl]imidazole)-diphenylmethylborane
(1-[bis(phenyl)-5-hexenylsilylmethyl]imidazole)-diphenylmethylborane
(1-[bis(phenyl)-1-methylpent-1-enylsilylmethyl]imidazole)-diphenylmethylborane
(1-[bis(phenyl)-1-methylpent-2-enylsilylmethyl]imidazole)-diphenylmethylborane
(1-[bis(phenyl)-1-methylpent-3-enylsilylmethyl]imidazole)-diphenylmethylborane
(1-[bis(phenyl)-1-methylpent-4-enylsilylmethyl]imidazole)-diphenylmethylborane
(1-[bis(phenyl)-2-methylpent-1-enylsilylmethyl]imidazole)-diphenylmethylborane
(1-[bis(phenyl)-2-methylpent-2-enylsilylmethyl]imidazole)-diphenylmethylborane
(1-[bis(phenyl)-2-methylpent-3-enylsilylmethyl]imidazole)-diphenylmethylborane
(1-[bis(phenyl)-2-methylpent-4-enylsilylmethyl]imidazole)-diphenylmethylborane
(1-[bis(phenyl)-3-methylpent-1-enylsilylmethyl]imidazole)-diphenylmethylborane
(1-[bis(phenyl)-3-methylpent-2-enylsilylmethyl]imidazole)-diphenylmethylborane
(1-[bis(phenyl)-3-methylpent-3-enylsilylmethyl]imidazole)-diphenylmethylborane
(1-[bis(phenyl)-4-methylpent-4-enylsilylmethyl]imidazole)-diphenylmethylborane
(1-[bis(phenyl)-1-ethylbut-1-enylsilylmethyl]imidazole)-diphenylmethylborane
(1-[bis(phenyl)-2-ethylbut-1-enylsilylmethyl]imidazole)-diphenylmethylborane
(1-[bis(phenyl)-4-methylphenylsilylmethyl]imidazole)-diphenylmethylborane
(1-[bis(phenyl)-4-ethylphenylsilylmethyl]imidazole)-diphenylmethylborane
(1-[bis(phenyl)-4-propylphenylsilylmethyl]imidazole)-diphenylmethylborane
(1-[bis(phenyl)-4-isopropylphenylsilylmethyl]imidazole)-diphenylmethylborane
(1-[bis(phenyl)-4-n-butylphenylsilylmethyl]imidazole)-diphenylmethylborane
(1-[bis(phenyl)-4-isobutylphenylsilylmethyl]imidazole)-diphenylmethylborane (1-[bis(phenyl)-4-t-butylphenylsilylmethyl]imidazole)-diphenylmethylborane
(1-[bis(phenyl)-4-n-pentylphenylsilylmethyl]imidazole)-diphenylmethylborane
(1-[bis(phenyl)-4-hexylphenylsilylmethyl]imidazole)-diphenylmethylborane
(1-[bis(phenyl)-4-chlorophenylsilylmethyl]imidazole)-diphenylmethylborane
(1-[bis(phenyl)-4-fluorophenylsilylmethyl]imidazole)-diphenylmethylborane
(1-[bis(phenyl)-4-methoxyphenylsilylmethyl]imidazole)-diphenylmethylborane
(1-[bis(phenyl)-4-ethoxyphenylsilylmethyl]imidazole)-diphenylmethylborane
(1-[bis(phenyl)-4-propoxyphenylsilylmethyl]imidazole)-diphenylmethylborane
(1-[bis(phenyl)-4-butoxyphenylsilylmethyl]imidazole)-diphenylmethylborane
(1-[bis(phenyl)-4-pentoxyphenylsilylmethyl]imidazole)-diphenylmethylborane
(1-[bis(phenyl)-4-hexoxyphenylsilylmethyl]imidazole)-diphenylmethylborane
(1-[bis(phenyl)-4-thiomethylphenylsilylmethyl]imidazole)-diphenylmethylborane
(1-[bis(phenyl)-4-thioethylphenylsilylmethyl]imidazole)-diphenylmethylborane
(1-[bis(phenyl)-4-thiopropylphenylsilylmethyl]imidazole)-diphenylmethylborane
(1-[bis(phenyl)-3-methylphenylsilylmethyl]imidazole)-diphenylmethylborane
(1-[bis(phenyl)-3-ethylphenylsilylmethyl]imidazole)-diphenylmethylborane
(1-[bis(phenyl)-3-propylphenylsilylmethyl]imidazole)-diphenylmethylborane
(1-[bis(phenyl)-3-isopropylphenylsilylmethyl]imidazole)-diphenylmethylborane
(1-[bis(phenyl)-3-n-butylphenylsilylmethyl]imidazole)-diphenylmethylborane
(1-[bis(phenyl)-3-isobutylphenylsilylmethyl]imidazole)-diphenylmethylborane
(1-[bis(phenyl)-3-t-butylphenylsilylmethyl]imidazole)-diphenylmethylborane
(1-[bis(phenyl)-3-n-pentylphenylsilylmethyl]imidazole)-diphenylmethylborane
(1-[bis(phenyl)-3-hexylphenylsilylmethyl]imidazole)-diphenylmethylborane
(1-[bis(phenyl)-3-chlorophenylsilylmethyl]imidazole)-diphenylmethylborane
(1-[bis(phenyl)-3-fluorophenylsilylmethyl]imidazole)-diphenylmethylborane
(1-[bis(phenyl)-3-methoxyphenylsilylmethyl]imidazole)-diphenylmethylborane
(1-[bis(phenyl)-3-ethoxyphenylsilylmethyl]imidazole)-diphenylmethylborane
(1-[bis(phenyl)-3-propoxyphenylsilylmethyl]imidazole)-diphenylmethylborane
(1-[bis(phenyl)-3-butoxyphenylsilylmethyl]imidazole)-diphenylmethylborane
(1-[bis(phenyl)-3-pentoxyphenylsilylmethyl]imidazole)-diphenylmethylborane
(1-[bis(phenyl)-3-hexoxyphenylsilylmethyl]imidazole)-diphenylmethylborane
(1-[bis(phenyl)-3-thiomethylphenylsilylmethyl]imidazole)-diphenylmethylborane
(1-[bis(phenyl)-3-thioethylphenylsilylmethyl]imidazole)-diphenylmethylborane
(1-[bis(phenyl)-3-thiopropylphenylsilylmethyl]imidazole)-diphenylmethylborane
(1-[triphenylsilylmethyl]imidazole)-diphenylvinylborane
(1-[bis(phenyl)methylsilylmethyl]imidazole)-diphenylvinylborane
(1-[bis(phenyl)ethylsilylmethyl]imidazole)-diphenylvinylborane
(1-[bis(phenyl)-n-propylsilylmethyl]imidazole)-diphenylvinylborane
(1-[bis(phenyl)-i-propylsilylmethyl]imidazole)-diphenylvinylborane
(1-[bis(phenyl)-n-butylsilylmethyl]imidazole)-diphenylvinylborane
(1-[bis(phenyl)-i-butylsilylmethyl]imidazole)-diphenylvinylborane
(1-[bis(phenyl)-t-butylsilylmethyl]imidazole)-diphenylvinylborane
(1-[bis(phenyl)cyclopropylsilylmethyl]imidazole)-diphenylvinylborane
(1-[bis(phenyl)cyclobutylsilylmethyl]imidazole)-diphenylvinylborane
(1-[bis(phenyl)cyclopentylsilylmethyl]imidazole)-diphenylvinylborane
(1-[bis(phenyl)cyclohexylsilylmethyl]imidazole)-diphenylvinylborane
(1-[bis(phenyl)vinylsilylmethyl]imidazole)-diphenylvinylborane
(1-[bis(phenyl)-1-propenylsilylmethyl]imidazole)-diphenylvinylborane
(1-[bis(phenyl)-2-propenylsilylmethyl]imidazole)-diphenylvinylborane
(1-[bis(phenyl)-1-methylvinylsilylmethyl]imidazole)-diphenylvinylborane
(1-[bis(phenyl)-1-butenylvinylsilylmethyl]imidazole)-diphenylvinylborane
(1-[bis(phenyl)-1-methylprop-1-enylsilylmethyl]imidazole)-diphenylvinylborane
(1-[bis(phenyl)-2-methylprop-1-enylsilylmethyl]imidazole)-diphenylvinylborane
(1-[bis(phenyl)-1-methylprop-2-enylsilylmethyl]imidazole)-diphenylvinylborane
(1-[bis(phenyl)-2-methylprop-2-enylsilylmethyl]imidazole)-diphenylvinylborane
(1-[bis(phenyl)-2-butenylsilylmethyl]imidazole)-diphenylvinylborane
(1-[bis(phenyl)-3-butenylsilylmethyl]imidazole)-diphenylvinylborane
(1-[bis(phenyl)-1-pentenylsilylmethyl]imidazole)-diphenylvinylborane
(1-[bis(phenyl)-2-pentenylsilylmethyl]imidazole)-diphenylvinylborane
(1-[bis(phenyl)-3-pentenylsilylmethyl]imidazole)-diphenylvinylborane
(1-[bis(phenyl)-4-pentenylsilylmethyl]imidazole)-diphenylvinylborane
(1-[bis(phenyl)-2-methylbut-2-enylsilylmethyl]imidazole)-diphenylvinylborane
(1-[bis(phenyl)-2-methylbut-3-enylsilylmethyl]imidazole)-diphenylvinylborane
(1-[bis(phenyl)-3-methylbut-1-enylsilylmethyl]imidazole)-diphenylvinylborane
(1-[bis(phenyl)-3-methylbut-2-enylsilylmethyl]imidazole)-diphenylvinylborane
(1-[bis(phenyl)-3-methylbut-3-enylsilylmethyl]imidazole)-diphenylvinylborane
(1-[bis(phenyl)-1-hexenylsilylmethyl]imidazole)-diphenylvinylborane
(1-[bis(phenyl)-2-hexenylsilylmethyl]imidazole)-diphenylvinylborane (1-[bis(phenyl)-3-hexenylsilylmethyl]imidazole)-
diphenylvinylborane
(1-[bis(phenyl)-4-hexenylsilylmethyl]imidazole)-
diphenylvinylborane
(1-[bis(phenyl)-5-hexenylsilylmethyl]imidazole)-
diphenylvinylborane
(1-[bis(phenyl)-1-methylpent-1-enylsilylmethyl-
]imidazole)-diphenylvinylborane
(1-[bis(phenyl)-1-methylpent-2-enylsilylmethyl-
]imidazole)-diphenylvinylborane
(1-[bis(phenyl)-1-methylpent-3-enylsilylmethyl-
]imidazole)-diphenylvinylborane
(1-[bis(phenyl)-1-methylpent-4-enylsilylmethyl-
]imidazole)-diphenylvinylborane
(1-[bis(phenyl)-2-methylpent-1-enylsilylmethyl-
]imidazole)-diphenylvinylborane
(1-[bis(phenyl)-2-methylpent-2-enylsilylmethyl-
]imidazole)-diphenylvinylborane
(1-[bis(phenyl)-2-methylpent-3-enylsilylmethyl-
]imidazole)-diphenylvinylborane
(1-[bis(phenyl)-2-methylpent-4-enylsilylmethyl-
]imidazole)-diphenylvinylborane
(1-[bis(phenyl)-3-methylpent-1-enylsilylmethyl-
]imidazole)-diphenylvinylborane
(1-[bis(phenyl)-3-methylpent-2-enylsilylmethyl-
]imidazole)-diphenylvinylborane
(1-[bis(phenyl)-3-methylpent-3-enylsilylmethyl-
]imidazole)-diphenylvinylborane
(1-[bis(phenyl)-4-methylpent-4-enylsilylmethyl-
]imidazole)-diphenylvinylborane
(1-[bis(phenyl)-1-ethylbut-1-enylsilylmethyl-
]imidazole)-diphenylvinylborane
(1-[bis(phenyl)-2-ethylbut-1-enylsilylmethyl-
]imidazole)-diphenylvinylborane
(1-[bis(phenyl)-4-methylphenylsilylmethyl]imidazole)-
diphenylvinylborane
(1-[bis(phenyl)-4-ethylphenylsilylmethyl]imidazole)-
diphenylvinylborane
(1-[bis(phenyl)-4-propylphenylsilylmethyl]imidazole)-
diphenylvinylborane
(1-[bis(phenyl)-4-isopropylphenylsilylmethyl-
]imidazole)-diphenylvinylborane
(1-[bis(phenyl)-4-n-butylphenylsilylmethyl]imidazole)-
diphenylvinylborane
(1-[bis(phenyl)-4-isobutylphenylsilylmethyl]imidazole)-
diphenylvinylborane
(1-[bis(phenyl)-4-t-butylphenylsilylmethyl]imidazole)-
diphenylvinylborane
(1-[bis(phenyl)-4-n-pentylphenylsilylmethyl]imidazole)-
diphenylvinylborane
(1-[bis(phenyl)-4-hexylphenylsilylmethyl]imidazole)-
diphenylvinylborane
(1-[bis(phenyl)-4-chlorophenylsilylmethyl]imidazole)-
diphenylvinylborane
(1-[bis(phenyl)-4-fluorophenylsilylmethyl]imidazole)-
diphenylvinylborane
(1-[bis(phenyl)-4-methoxyphenylsilylmethyl-
]imidazole)-diphenylvinylborane
(1-[bis(phenyl)-4-ethoxyphenylsilylmethyl]imidazole)-
diphenylvinylborane
(1-[bis(phenyl)-4-propoxyphenylsilylmethyl-
]imidazole)-diphenylvinylborane
(1-[bis(phenyl)-4-butoxyphenylsilylmethyl]imidazole)-
diphenylvinylborane
(1-[bis(phenyl)-4-pentoxyphenylsilylmethyl]imidazole)-
diphenylvinylborane
(1-[bis(phenyl)-4-hexoxyphenylsilylmethyl]imidazole)-
diphenylvinylborane
(1-[bis(phenyl)-4-thiomethylphenylsilylmethyl-
]imidazole)-diphenylvinylborane
(1-[bis(phenyl)-4-thioethylphenylsilylmethyl-
]imidazole)-diphenylvinylborane
(1-[bis(phenyl)-4-thiopropylphenylsilylmethyl-
]imidazole)-diphenylvinylborane
(1-[bis(phenyl)-3-methylphenylsilylmethyl-
]imidazole)-diphenylvinylborane
(1-[bis(phenyl)-3-ethylphenylsilylmethyl]imidazole)-
diphenylvinylborane
(1-[bis(phenyl)-3-propylphenylsilylmethyl]imidazole)-
diphenylvinylborane
(1-[bis(phenyl)-3-isopropylphenylsilylmethyl-
]imidazole)-diphenylvinylborane
(1-[bis(phenyl)-3-n-butylphenylsilylmethyl]imidazole)-
diphenylvinylborane
(1-[bis(phenyl)-3-isobutylphenylsilylmethyl]imidazole)-
diphenylvinylborane
(1-[bis(phenyl)-3-t-butylphenylsilylmethyl]imidazole)-
diphenylvinylborane
(1-[bis(phenyl)-3-n-pentylphenylsilylmethyl]imidazole)-
diphenylvinylborane
(1-[bis(phenyl)-3-hexylphenylsilylmethyl]imidazole)-
diphenylvinylborane
(1-[bis(phenyl)-3-chlorophenylsilylmethyl]imidazole)-
diphenylvinylborane
(1-[bis(phenyl)-3-fluorophenylsilylmethyl]imidazole)-
diphenylvinylborane
(1-[bis(phenyl)-3-methoxyphenylsilylmethyl-
]imidazole)-diphenylvinylborane
(1-[bis(phenyl)-3-ethoxyphenylsilylmethyl]imidazole)-
diphenylvinylborane
(1-[bis(phenyl)-3-propoxyphenylsilylmethyl-
]imidazole)-diphenylvinylborane
(1-[bis(phenyl)-3-butoxyphenylsilylmethyl]imidazole)-
diphenylvinylborane
(1-[bis(phenyl)-3-pentoxyphenylsilylmethyl]imidazole)-
diphenylvinylborane
(1-[bis(phenyl)-3-hexoxyphenylsilylmethyl]imidazole)-
diphenylvinylborane
(1-[bis(phenyl)-3-thiomethylphenylsilylmethyl-
]imidazole)-diphenylvinylborane
(1-[bis(phenyl)-3-thioethylphenylsilylmethyl-
]imidazole)-diphenylvinylborane
(1-[bis(phenyl)-3-thiopropylphenylsilylmethyl-
]imidazole)-diphenylvinylborane
(1-[triphenylsilylmethyl]imidazole)-diphenylcyclo-
propylborane
(1-[bis(phenyl)methylsilylmethyl]imidazole)-diphenyl-
cyclopropylborane
(1-[bis(phenyl)ethylsilylmethyl]imidazole)-diphenylcy-
clopropylborane
(1-[bis(phenyl)-n-propylsilylmethyl]imidazole)-
diphenylcyclopropylborane
(1-[bis(phenyl)-i-propylsilylmethyl]imidazole)-
diphenylcyclopropylborane
(1-[bis(phenyl)-n-butylsilylmethyl]imidazole)-diphenyl-
cyclopropylborane
(1-[bis(phenyl)-i-butylsilylmethyl]imidazole)-diphenyl-
cyclopropylborane
(1-[bis(phenyl)-t-butylsilylmethyl]imidazole)-diphenyl-
cyclopropylborane
(1-[bis(phenyl)cyclopropylsilylmethyl]imidazole)-
diphenylcyclopropylborane
(1-[bis(phenyl)cylcobutylsilylmethyl]imidazole)-
diphenylcyclopropylborane
(1-[bis(phenyl)cyclopentylsilylmethyl]imidazole)-
diphenylcyclopropylborane (1-[bis(phenyl)cyclohexylsilylmethyl]imidazole)-diphenylcyclopropylborane
(1-[bis(phenyl)vinylsilylmethyl]imidazole)-diphenylcyclopropylborane
(1-[bis(phenyl)-1-propenylsilylmethyl]imidazole)-diphenylcyclopropylborane
(1-[bis(phenyl)-2-propenylsilylmethyl]imidazole)-diphenylcyclopropylborane
(1-[bis(phenyl)-1-methylvinylsilylmethyl]imidazole)-diphenylcyclopropylborane
(1-[bis(phenyl)-1-butenylvinylsilylmethyl]imidazole)-diphenylcyclopropylborane
(1-[bis(phenyl)-1-methylprop-1-enylsilylmethyl]imidazole)-diphenylcyclopropylborane
(1-[bis(phenyl)-2-methylprop-1-enylsilylmethyl]imidazole)-diphenylcyclopropylborane
(1-[bis(phenyl)-1-methylprop-2-enylsilylmethyl]imidazole)-diphenylcyclopropylborane
(1-[bis(phenyl)-2-methylprop-2-enylsilylmethyl]imidazole)-diphenylcyclopropylborane
(1-[bis(phenyl)-2-butenylsilylmethyl]imidazole)-diphenylcyclopropylborane
(1-[bis(phenyl)-3-butenylsilylmethyl]imidazole)-diphenylcyclopropylborane
(1-[bis(phenyl)-1-pentenylsilylmethyl]imidazole)-diphenylcyclopropylborane
(1-[bis(phenyl)-2-pentenylsilylmethyl]imidazole)-diphenylcyclopropylborane
(1-[bis(phenyl)-3-pentenylsilylmethyl]imidazole)-diphenylcyclopropylborane
(1-[bis(phenyl)-4-pentenylsilylmethyl]imidazole)-diphenylcyclopropylborane
(1-[bis(phenyl)-2-methylbut-2-enylsilylmethyl]imidazole)-diphenylcyclopropylborane
(1-[bis(phenyl)-2-methylbut-3-enylsilylmethyl]imidazole)-diphenylcyclopropylborane
(1-[bis(phenyl)-3-methylbut-1-enylsilylmethyl]imidazole)-diphenylcyclopropylborane
(1-[bis(phenyl)-3-methylbut-2-enylsilylmethyl]imidazole)-diphenylcyclopropylborane
(1-[bis(phenyl)-3-methylbut-3-enylsilylmethyl]imidazole)-diphenylcyclopropylborane
(1-[bis(phenyl)-1-hexenylsilylmethyl]imidazole)-diphenylcyclopropylborane
(1-[bis(phenyl)-2-hexenylsilylmethyl]imidazole)-diphenylcyclopropylborane
(1-[bis(phenyl)-3-hexenylsilylmethyl]imidazole)-diphenylcyclopropylborane
(1-[bis(phenyl)-4-hexenylsilylmethyl]imidazole)-diphenylcyclopropylborane
(1-[bis(phenyl)-5-hexenylsilylmethyl]imidazole)-diphenylcyclopropylborane
(1-[bis(phenyl)-1-methylpent-1-enylsilylmethyl]imidazole)-diphenylcyclopropylborane
(1-[bis(phenyl)-1-methylpent-2-enylsilylmethyl]imidazole)-diphenylcyclopropylborane
(1-[bis(phenyl)-1-methylpent-3-enylsilylmethyl]imidazole)-diphenylcyclopropylborane
(1-[bis(phenyl)-1-methylpent-4-enylsilylmethyl]imidazole)-diphenylcyclopropylborane
(1-[bis(phenyl)-2-methylpent-1-enylsilylmethyl]imidazole)-diphenylcyclopropylborane
(1-[bis(phenyl)-2-methylpent-2-enylsilylmethyl]imidazole)-diphenylcyclopropylborane
(1-[bis(phenyl)-2-methylpent-3-enylsilylmethyl]imidazole)-diphenylcyclopropylborane
(1-[bis(phenyl)-2-methylpent-4-enylsilylmethyl]imidazole)-diphenylcyclopropylborane
(1-[bis(phenyl)-3-methylpent-1-enylsilylmethyl]imidazole)-diphenylcyclopropylborane
(1-[bis(phenyl)-3-methylpent-2-enylsilylmethyl]imidazole)-diphenylcyclopropylborane
(1-[bis(phenyl)-3-methylpent-3-enylsilylmethyl]imidazole)-diphenylcyclopropylborane
(1-[bis(phenyl)-4-methylpent-4-enylsilylmethyl]imidazole)-diphenylcyclopropylborane
(1-[bis(phenyl)-1-ethylbut-1-enylsilylmethyl]imidazole)-diphenylcyclopropylborane
(1-[bis(phenyl)-2-ethylbut-1-enylsilylmethyl]imidazole)-diphenylcyclopropylborane
(1-[bis(phenyl)-4-methylphenylsilylmethyl]imidazole)-diphenylcyclopropylborane
(1-[bis(phenyl)-4-ethylphenylsilylmethyl]imidazole)-diphenylcyclopropylborane
(1-[bis(phenyl)-4-propylphenylsilylmethyl]imidazole)-diphenylcyclopropylborane
(1-[bis(phenyl)-4-isopropylphenylsilylmethyl]imidazole)-diphenylcyclopropylborane
(1-[bis(phenyl)-4-n-butylphenylsilylmethyl]imidazole)-diphenylcyclopropylborane
(1-[bis(phenyl)-4-isobutylphenylsilylmethyl]imidazole)-diphenylcyclopropylborane
(1-[bis(phenyl)-4-t-butylphenylsilylmethyl]imidazole)-diphenylcyclopropylborane
(1-[bis(phenyl)-4-n-pentylphenylsilylmethyl]imidazole)-diphenylcyclopropylborane
(1-[bis(phenyl)-4-hexylphenylsilylmethyl]imidazole)-diphenylcyclopropylborane
(1-[bis(phenyl)-4-chlorophenylsilylmethyl]imidazole)-diphenylcyclopropylborane
(1-[bis(phenyl)-4-fluorophenylsilylmethyl]imidazole)-diphenylcyclopropylborane
(1-[bis(phenyl)-4-methoxyphenylsilylmethyl]imidazole)-diphenylcyclopropylborane
(1-[bis(phenyl)-4-ethoxyphenylsilylmethyl]imidazole)-diphenylcyclopropylborane
(1-[bis(phenyl)-4-propoxyphenylsilylmethyl]imidazole)-diphenylcyclopropylborane
(1-[bis(phenyl)-4-butoxyphenylsilylmethyl]imidazole)-diphenylcyclopropylborane
(1-[bis(phenyl)-4-pentoxyphenylsilylmethyl]imidazole)-diphenylcyclopropylborane
(1-[bis(phenyl)-4-hexoxyphenylsilylmethyl]imidazole)-diphenylcyclopropylborane
(1-[bis(phenyl)-4-thiomethylphenylsilylmethyl]imidazole)-diphenylcyclopropylborane
(1-[bis(phenyl)-4-thioethylphenylsilylmethyl]imidazole)-diphenylcyclopropylborane
(1-[bis(phenyl)-4-thiopropylphenylsilylmethyl]imidazole)-diphenylcyclopropylborane
(1-[bis(phenyl)-3-methylphenylsilylmethyl]imidazole)-diphenylcyclopropylborane
(1-[bis(phenyl)-3-ethylphenylsilylmethyl]imidazole)-diphenylcyclopropylborane
(1-[bis(phenyl)-3-propylphenylsilylmethyl]imidazole)-diphenylcyclopropylborane
(1-[bis(phenyl)-3-isopropylphenylsilylmethyl]imidazole)-diphenylcyclopropylborane
(1-[bis(phenyl)-3-n-butylphenylsilylmethyl]imidazole)-diphenylcyclopropylborane
(1-[bis(phenyl)-3-isobutylphenylsilylmethyl]imidazole)-diphenylcyclopropylborane
(1-[bis(phenyl)-3-t-butylphenylsilylmethyl]imidazole)-diphenylcyclopropylborane
(1-[bis(phenyl)-3-n-pentylphenylsilylmethyl]imidazole)-diphenylcyclopropylborane (1-[bis(phenyl)-3-hexylphenylsilylmethyl]imidazole)-diphenylcyclopropylborane
(1-[bis(phenyl)-3-chlorophenylsilylmethyl]imidazole)-diphenylcyclopropylborane
(1-[bis(phenyl)-3-fluorophenylsilylmethyl]imidazole)-diphenylcyclopropylborane
(1-[bis(phenyl)-3-methoxyphenylsilylmethyl]imidazole)-diphenylcyclopropylborane
(1-[bis(phenyl)-3-ethoxyphenylsilylmethyl]imidazole)-diphenylcyclopropylborane
(1-[bis(phenyl)-3-propoxyphenylsilylmethyl]imidazole)-diphenylcyclopropylborane
(1-[bis(phenyl)-3-butoxyphenylsilylmethyl]imidazole)-diphenylcyclopropylborane
(1-[bis(phenyl)-3-pentoxyphenylsilylmethyl]imidazole)-diphenylcyclopropylborane
(1-[bis(phenyl)-3-hexoxyphenylsilylmethyl]imidazole)-diphenylcyclopropylborane
(1-[bis(phenyl)-3-thiomethylphenylsilylmethyl]imidazole)-diphenylcyclopropylborane
(1-[bis(phenyl)-3-thioethylphenylsilylmethyl]imidazole)-diphenylcyclopropylborane
(1-[bis(phenyl)-3-thiopropylphenylsilylmethyl]imidazole)-diphenylcyclopropylborane
(1-[bis(4-methylphenyl)phenylsilylmethyl]imidazole)-diphenylmethylborane
(1-[bis(4-ethylphenyl)phenylsilylmethyl]imidazole)-diphenylmethylborane
(1-[bis(4-propylphenyl)phenylsilylmethyl]imidazole)-diphenylmethylborane
(1-[bis(4-isopropylphenyl)phenylsilylmethyl]imidazole)-diphenylmethylborane
(1-[bis(4-n-butylphenyl)phenylsilylmethyl]imidazole)-diphenylmethylborane
(1-[bis(4-isobutylphenyl)phenylsilylmethyl]imidazole)-diphenylmethylborane
(1-[bis(4-t-butylphenyl)phenylsilylmethyl]imidazole)-diphenylmethylborane
(1-[bis(4-n-pentylphenyl)phenylsilylmethyl]imidazole)-diphenylmethylborane
(1-[bis(4-hexylphenyl)phenylsilylmethyl]imidazole)-diphenylmethylborane
(1-[bis(4-chlorophenyl)phenylsilylmethyl]imidazole)-diphenylmethylborane
(1-[bis(4-fluorophenyl)phenylsilylmethyl]imidazole)-diphenylmethylborane
(1-[bis(4-methoxyphenyl)phenylsilylmethyl]imidazole)-diphenylmethylborane
(1-[bis(4-ethoxyphenyl)phenylsilylmethyl]imidazole)-diphenylmethylborane
(1-[bis(4-propoxyphenyl)phenylsilylmethyl]imidazole)-diphenylmethylborane
(1-[bis(4-butoxyphenyl)phenylsilylmethyl]imidazole)-diphenylmethylborane
(1-[bis(4-pentoxyphenyl)phenylsilylmethyl]imidazole)-diphenylmethylborane
(1-[bis(4-hexoxyphenyl)phenylsilylmethyl]imidazole)-diphenylmethylborane
(1-[bis(4-thiomethylphenyl)phenylsilylmethyl]imidazole)-diphenylmethylborane
(1-[bis(4-thioethylphenyl)phenylsilylmethyl]imidazole)-diphenylmethylborane
(1-[bis(4-thiopropylphenyl)phenylsilylmethyl]imidazole)-diphenylmethylborane
(1-[bis(3-methylphenyl)phenylsilylmethyl]imidazole)-diphenylmethylborane
(1-[bis(3-ethylphenyl)phenylsilylmethyl]imidazole)-diphenylmethylborane
(1-[bis(3-propylphenyl)phenylsilylmethyl]imidazole)-diphenylmethylborane
(1-[bis(3-isopropylphenyl)phenylsilylmethyl]imidazole)-diphenylmethylborane
(1-[bis(3-n-butylphenyl)phenylsilylmethyl]imidazole)-diphenylmethylborane
(1-[bis(3-isobutylphenyl)phenylsilylmethyl]imidazole)-diphenylmethylborane
(1-[bis(3-t-butylphenyl)phenylsilylmethyl]imidazole)-diphenylmethylborane
(1-[bis(3-n-pentylphenyl)phenylsilylmethyl]imidazole)-diphenylmethylborane
(1-[bis(3-hexylphenyl)phenylsilylmethyl]imidazole)-diphenylmethylborane
(1-[bis(3-chlorophenyl)phenylsilylmethyl]imidazole)-diphenylmethylborane
(1-[bis(3-fluorophenyl)phenylsilylmethyl]imidazole)-diphenylmethylborane
(1-[bis(3-methoxyphenyl)phenylsilylmethyl]imidazole)-diphenylmethylborane
(1-[bis(3-ethoxyphenyl)phenylsilylmethyl]imidazole)-diphenylmethylborane
(1-[bis(3-propoxyphenyl)phenylsilylmethyl]imidazole)-diphenylmethylborane
(1-[bis(3-butoxyphenyl)phenylsilylmethyl]imidazole)-diphenylmethylborane
(1-[bis(3-pentoxyphenyl)phenylsilylmethyl]imidazole)-diphenylmethylborane
(1-[bis(3-hexoxyphenyl)phenylsilylmethyl]imidazole)-diphenylmethylborane
(1-[bis(3-thiomethylphenyl)phenylsilylmethyl]imidazole)-diphenylmethylborane
(1-[bis(3-thioethylphenyl)phenylsilylmethyl]imidazole)-diphenylmethylborane
(1-[bis(3-thiopropylphenyl)phenylsilylmethyl]imidazole)-diphenylmethylborane

EXAMPLE 3

[1-Bis(4-fluorophenyl)methylsilylmethyl-1H-1,2,4-triazole]-diphenylmethylborane

The title compound can be prepared by adding 18.0 mL of 1.0 M methylmagnesium bromide in THF dropwise under a $N_2$ atmosphere to 2-amino-ethyldiphenyl borinate (Prep. C). This mixture is heated to reflux for two hours, then allowed to cool to room temperature for two hours. Next, a 2.00 g amount of 1-[bis(4-fluorophenyl)methylsilylmethyl]-1H-1,2,4-triazole is added and the solution is stirred overnight. The next day, 100 mL of a 5% solution of HCl and 200 mL of diethyl ether are added. The ether layer is removed and the aqueous layer is extracted twice more with 50-mL portions of diethyl ether. The ether layers are combined and dried over magnesium sulfate. After removal of the diethyl ether, 100 mL of ethanol is added and a white precipitate forms, with a melting point of 126°–127° C.

Similarly, by applying the above referenced procedure using the appropriate starting materials, the following compounds can be prepared:
[1-triphenylsilylmethyl-1H-1,2,4-triazole]-diphenylmethylborane
[1-bis(phenyl)methtylsilylmethyl-1H- 1,2,4-triazole]-diphenylmethylborane
[1-bis(phenyl)ethylsilylmethyl-1H-1,2,4-triazole]-diphenylmethylborane
[1-bis(phenyl)-n-propylsilylmethyl-1H-1,2,4-triazole]-diphenylmethylborane

[1-bis(phenyl)-i-propylsilylmethyl-1H-1,2,4-triazole]-
diphenylmethylborane
[1-bis(phenyl)-n-butylsilylmethyl-1H-1,2,4-triazole]-
diphenylmethylborane
[1-bis(phenyl)-i-butylsilylmethyl-1H-1,2,4-triazole]-
diphenylmethylborane
[1-bis(phenyl)-t-butylsilylmethyl-1H-1,2,4-triazole]-
diphenylmethylborane
[1-bis(phenyl)cyclopropylsilylmethyl-1H-1,2,4-
triazole]-diphenylmethylborane
[1-bis(phenyl)cyclobutylsilylmethyl-1H-1,2,4-triazole]-
diphenylmethylborane
[1-bis(phenyl)cyclopentylsilylmethyl-1H-1,2,4-
triazole]-diphenylmethylborane
[1-bis(phenyl)cyclohexylsilylmethyl-1H-1,2,4-triazole]-
diphenylmethylborane
[1-bis(phenyl)vinylsilylmethyl-1H-1,2,4-triazole]-
diphenylmethylborane
[1-bis(phenyl)-1-propenylsilylmethyl-1H-1,2,4-
triazole]-diphenylmethylborane
[1-bis(phenyl)-2-propenylsilylmethyl-1H-1,2,4-
triazole]-diphenylmethylborane
[1-bis(phenyl)-1-methylvinylsilylmethyl-1H-1,2,4-
triazole]-diphenylmethylborane
[1-bis(phenyl)-1-butenylvinylsilylmethyl-1H-1,2,4-
triazole]-diphenylmethylborane
[1-bis(phenyl)-1-methylprop-1-enylsilylmethyl-1H-
1,2,4-triazole]-diphenylmethylborane
[1-bis(phenyl)-2-methylprop-1-enylsilylmethyl-1H-
1,2,4-triazole]-diphenylmethylborane
[1-bis(phenyl)-1-methylprop-2-enylsilylmethyl-1H-
1,2,4-triazole]-diphenylmethylborane
[1-bis(phenyl)-2-methylprop-2-enylsilylmethyl-1H-
1,2,4-triazole]-diphenylmethylborane
[1-bis(phenyl)-2-butenylsilylmethyl-1H-1,2,4-triazole]-
diphenylmethylborane
[1-bis(phenyl)-3-butenylsilylmethyl-1H-1,2,4-triazole]-
diphenylmethylborane
[1-bis(phenyl)-1-pentenylsilylmethyl-1H-1,2,4-triazole]-
diphenylmethylborane
[1-bis(phenyl)-2-pentenylsilylmethyl-1H-1,2,4-triazole]-
diphenylmethylborane
[1-bis(phenyl)-3-pentenylsilylmethyl-1H-1,2,4-triazole]-
diphenylmethylborane
[1-bis(phenyl)-4-pentenylsilylmethyl-1H-1,2,4-triazole]-
diphenylmethylborane
[1-bis(phenyl)-2-methylbut-2-enylsilylmethyl-1H-1,2,4-
triazole]-diphenylmethylborane
[1-bis(phenyl)-2-methylbut-3-enylsilylmethyl-1H-1,2,4-
triazole]-diphenylmethylborane
[1-bis(phenyl)-3-methylbut-1-enylsilylmethyl-1H-1,2,4-
triazole]-diphenylmethylborane
[1-bis(phenyl)-3-methylbut-2-enylsilylmethyl-1H-1,2,4-
triazole]-diphenylmethylborane
[1-bis(phenyl)-3-methylbut-3-enylsilylmethyl-1H-1,2,4-
triazole]-diphenylmethylborane
[1-bis(phenyl)-1-hexenylsilylmethyl-1H-1,2,4-triazole]-
diphenylmethylborane
[1-bis(phenyl)-2-hexenylsilylmethyl-1H-1,2,4-triazole]-
diphenylmethylborane
[1-bis(phenyl)-3-hexenylsilylmethyl-1H-1,2,4-triazole]-
diphenylmethylborane
[1-bis(phenyl)-4-hexenylsilylmethyl-1H-1,2,4-triazole]-
diphenylmethylborane
[1-bis(phenyl)-5-hexenylsilylmethyl-1H-1,2,4-triazole]-
diphenylmethylborane
[1-bis(phenyl)-1-methylpent-1-enylsilylmethyl-1H-
1,2,4-triazole]-diphenylmethylborane
[1-bis(phenyl)-1-methylpent-2-enylsilylmethyl-1H-
1,2,4-triazole]-diphenylmethylborane
[1-bis(phenyl)-1-methylpent-3-enylsilylmethyl-1H-
1,2,4-triazole]-diphenylmethylborane
[1-bis(phenyl)-1-methylpent-4-enylsilylmethyl-1H-
1,2,4-triazole]-diphenylmethylborane
[1-bis(phenyl)-2-methylpent-1-enylsilylmethyl-1H-
1,2,4-triazole]-diphenylmethylborane
[1-bis(phenyl)-2-methylpent-2-enylsilylmethyl-1H-
1,2,4-triazole]-diphenylmethylborane
[1-bis(phenyl)-2-methylpent-3-enylsilylmethyl-1H-
1,2,4-triazole]-diphenylmethylborane
[1-bis(phenyl)-2-methylpent-4-enylsilylmethyl-1H-
1,2,4-triazole]-diphenylmethylborane
[1-bis(phenyl)-3-methylpent-1-enylsilylmethyl-1H-
1,2,4-triazole]-diphenylmethylborane
[1-bis(phenyl)-3-methylpent-2-enylsilylmethyl-1H-
1,2,4-triazole]-diphenylmethylborane
[1-bis(phenyl)-3-methylpent-3-enylsilylmethyl-1H-
1,2,4-triazole]-diphenylmethylborane
[1-bis(phenyl)-4-methylpent-4-enylsilylmethyl-1H-
1,2,4-triazole]-diphenylmethylborane
[1-bis(phenyl)-1-ethylbut-1-enylsilylmethyl-1H-1,2,4-
triazole]-diphenylmethylborane
[1-bis(phenyl)-2-ethylbut-1-enylsilylmethyl-1H-1,2,4-
triazole]-diphenylmethylborane
[1-bis(phenyl)-4-methylphenylsilylmethyl-1H-1,2,4-
triazole]-diphenylmethylborane
[1-bis(phenyl)-4-ethylphenylsilylmethyl-1H-1,2,4-
triazole]-diphenylmethylborane
[1-bis(phenyl)-4-propylphenylsilylmethyl-1H-1,2,4-
triazole]-diphenylmethylborane
[1-bis(phenyl)-4-isopropylphenylsilylmethyl-1H-1,2,4-
triazole]-diphenylmethylborane
[1-bis(phenyl)-4-n-butylphenylsilylmethyl-1H-1,2,4-
triazole]-diphenylmethylborane
[1-bis(phenyl)-4-isobutylphenylsilylmethyl-1H-1,2,4-
triazole]-diphenylmethylborane
[1-bis(phenyl)-4-t-butylphenylsilylmethyl-1H-1,2,4-
triazole]-diphenylmethylborane
[1-bis(phenyl)-4-n-pentylphenylsilylmethyl-1H-1,2,4-
triazole]-diphenylmethylborane
[1-bis(phenyl)-4-hexylphenylsilylmethyl-1H-1,2,4-
triazole]-diphenylmethylborane
[1-bis(phenyl)-4-chlorophenylsilylmethyl-1H-1,2,4-
triazole]-diphenylmethylborane
[1-bis(phenyl)-4-fluorophenylsilylmethyl-1H-1,2,4-
triazole]-diphenylmethylborane
[1-bis(phenyl)-4-methoxyphenylsilylmethyl-1H-1,2,4-
triazole]-diphenylmethylborane
[1-bis(phenyl)-4-ethoxyphenylsilylmethyl-1H-1,2,4-
triazole]-diphenylmethylborane
[1-bis(phenyl)-4-propoxyphenylsilylmethyl-1H-1,2,4-
triazole]-diphenylmethylborane
[1-bis(phenyl)-4-butoxyphenylsilylmethyl-1H-1,2,4-
triazole]-diphenylmethylborane
[1-bis(phenyl)-4-pentoxyphenylsilylmethyl-1H-1,2,4-
triazole]-diphenylmethylborane
[1-bis(phenyl)-4-hexoxyphenylsilylmethyl-1H-1,2,4-
triazole]-diphenylmethylborane
[1-bis(phenyl)-4-thiomethylphenylsilylmethyl-1H-1,2,4-
triazole]-diphenylmethylborane
[1-bis(phenyl)-4-thioethylphenylsilylmethyl-1H-1,2,4-
triazole]-diphenylmethylborane
[1-bis(phenyl)-4-thiopropylphenylsilylmethyl-1H-1,2,4-
triazole]-diphenylmethylborane
[1-bis(phenyl)-3-methylphenylsilylmethyl-1H-1,2,4-
triazole]-diphenylmethylborane

[1-bis(phenyl)-3-ethylphenylsilylmethyl-1H-1,2,4-triazole]-diphenylmethylborane
[1-bis(phenyl)-3-propylphenylsilylmethyl-1H-1,2,4-triazole]-diphenylmethylborane
[1-bis(phenyl)-3-isopropylphenylsilylmethyl-1H-1,2,4-triazole]-diphenylmethylborane
[1-bis(phenyl)-3-n-butylphenylsilylmethyl-1H-1,2,4-triazole]-diphenylmethylborane
[1-bis(phenyl)-3-isobutylphenylsilylmethyl-1H-1,2,4-triazole]-diphenylmethylborane
[1-bis(phenyl)-3-t-butylphenylsilylmethyl-1H-1,2,4-triazole]-diphenylmethylborane
[1-bis(phenyl)-3-n-pentylphenylsilylmethyl-1H-1,2,4-triazole]-diphenylmethylborane
[1-bis(phenyl)-3-hexylphenylsilylmethyl-1H-1,2,4-triazole]-diphenylmethylborane
[1-bis(phenyl)-3-chlorophenylsilylmethyl-1H-1,2,4-triazole]-diphenylmethylborane
[1-bis(phenyl)-3-fluorophenylsilylmethyl-1H-1,2,4-triazole]-diphenylmethylborane
[1-bis(phenyl)-3-methoxyphenylsilylmethyl-1H-1,2,4-triazole]-diphenylmethylborane
[1-bis(phenyl)-3-ethoxyphenylsilylmethyl-1H-1,2,4-triazole]-diphenylmethylborane
[1-bis(phenyl)-3-propoxyphenylsilylmethyl-1H-1,2,4-triazole]-diphenylmethylborane
[1-bis(phenyl)-3-butoxyphenylsilylmethyl-1H-1,2,4-triazole]-diphenylmethylborane
[1-bis(phenyl)-3-pentoxyphenylsilylmethyl-1H-1,2,4-triazole]-diphenylmethylborane
[1-bis(phenyl)-3-hexoxyphenylsilylmethyl-1H-1,2,4-triazole]-diphenylmethylborane
[1-bis(phenyl)-3-thiomethylphenylsilylmethyl-1H-1,2,4-triazole]-diphenylmethylborane
[1-bis(phenyl)-3-thioethylphenylsilylmethyl-1H-1,2,4-triazole]-diphenylmethylborane
[1-bis(phenyl)-3-thiopropylphenylsilylmethyl-1H-1,2,4-triazole]-diphenylmethylborane
[1-triphenylsilylmethyl-1H-1,2,4-triazole]-diphenylvinylborane
[1-bis(phenyl)methylsilylmethyl-1H-1,2,4-triazole]-diphenylvinylborane
[1-bis(phenyl)ethylsilylmethyl-1H-1,2,4-triazole]-diphenylvinylborane
[1-bis(phenyl)-n-propylsilylmethyl-1H-1,2,4-triazole]-diphenylvinylborane
[1-bis(phenyl)-i-propylsilylmethyl-1H-1,2,4-triazole]-diphenylvinylborane
[1-bis(phenyl)-n-butylsilylmethyl-1H-1,2,4-triazole]-diphenylvinylborane
[1-bis(phenyl)-i-butylsilylmethyl-1H-1,2,4-triazole]-diphenylvinylborane
[1-bis(phenyl)-t-butylsilylmethyl-1H-1,2,4-triazole]-diphenylvinylborane
[1-bis(phenyl)cyclopropylsilylmethyl-1H-1,2,4-triazole]-diphenylvinylborane
[1-bis(phenyl)cylcobutylsilylmethyl-1H-1,2,4-triazole]-diphenylvinylborane
[1-bis(phenyl)cyclopentylsilylmethyl-1H-1,2,4-triazole]-diphenylvinylborane
[1-bis(phenyl)cyclohexylsilylmethyl-1H-1,2,4-triazole]-diphenylvinylborane
[1-bis(phenyl)vinylsilylmethyl-1H-1,2,4-triazole]-diphenylvinylborane
[1-bis(phenyl)-1-propenylsilylmethyl-1H-1,2,4-triazole]-diphenylvinylborane
[1-bis(phenyl)-2-propenylsilylmethyl-1H-1,2,4-triazole]-diphenylvinylborane
[1-bis(phenyl)-1-methylvinylsilylmethyl-1H-1,2,4-triazole]-diphenylvinylborane
[1-bis(phenyl)-1-butenylvinylsilylmethyl-1H-1,2,4-triazole]-diphenylvinylborane
[1-bis(phenyl)-1-methylprop-1-enylsilylmethyl-1H-1,2,4-triazole]-diphenylvinylborane
[1-bis(phenyl)-2-methylprop-1-enylsilylmethyl-1H-1,2,4-triazole]-diphenylvinylborane
[1-bis(phenyl)-1-methylprop-2-enylsilylmethyl-1H-1,2,4-triazole]-diphenylvinylborane
[1-bis(phenyl)-2-methylprop-2-enylsilylmethyl-1H-1,2,4-triazole]-diphenylvinylborane
[1-bis(phenyl)-2-butenylsilylmethyl-1H-1,2,4-triazole]-diphenylvinylborane
[1-bis(phenyl)-3-butenylsilylmethyl-1H-1,2,4-triazole]-diphenylvinylborane
[1-bis(phenyl)-1-pentenylsilylmethyl-1H-1,2,4-triazole]-diphenylvinylborane
[1-bis(phenyl)-2-pentenylsilylmethyl-1H-1,2,4-triazole]-diphenylvinylborane
[1-bis(phenyl)-3-pentenylsilylmethyl-1H-1,2,4-triazole]-diphenylvinylborane
[1-bis(phenyl)-4-pentenylsilylmethyl-1H-1,2,4-triazole]-diphenylvinylborane
[1-bis(phenyl)-2-methylbut-2-enylsilylmethyl-1H-1,2,4-triazole]-diphenylvinylborane
[1-bis(phenyl)-2-methylbut-3-enylsilylmethyl-1H-1,2,4-triazole]-diphenylvinylborane
[1-bis(phenyl)-3-methylbut-1-enylsilylmethyl-1H-1,2,4-triazole]-diphenylvinylborane
[1-bis(phenyl)-3-methylbut-2-enylsilylmethyl-1H-1,2,4-triazole]-diphenylvinylborane
[1-bis(phenyl)-3-methylbut-3-enylsilylmethyl-1H-1,2,4-triazole]-diphenylvinylborane
[1-bis(phenyl)-1-hexenylsilylmethyl-1H-1,2,4-triazole]-diphenylvinylborane
[1-bis(phenyl)-2-hexenylsilylmethyl-1H-1,2,4-triazole]-diphenylvinylborane
[1-bis(phenyl)-3-hexenylsilylmethyl-1H-1,2,4-triazole]-diphenylvinylborane
[1-bis(phenyl)-4-hexenylsilylmethyl-1H-1,2,4-triazole]-diphenylvinylborane
[1-bis(phenyl)-5-hexenylsilylmethyl-1H-1,2,4-triazole]-diphenylvinylborane
[1-bis(phenyl)-1-methylpent-1-enylsilylmethyl-1H-1,2,4-triazole]-diphenylvinylborane
[1-bis(phenyl)-1-methylpent-2-enylsilylmethyl-1H-1,2,4-triazole]-diphenylvinylborane
[1-bis(phenyl)-1-methylpent-3-enylsilylmethyl-1H-1,2,4-triazole]-diphenylvinylborane
[1-bis(phenyl)-1-methylpent-4-enylsilylmethyl-1H-1,2,4-triazole]-diphenylvinylborane
[1-bis(phenyl)-2-methylpent-1-enylsilylmethyl-1H-1,2,4-triazole]-diphenylvinylborane
[1-bis(phenyl)-2-methylpent-2-enylsilylmethyl-1H-1,2,4-triazole]-diphenylvinylborane
[1-bis(phenyl)-2-methylpent-3-enylsilylmethyl-1H-1,2,4-triazole]-diphenylvinylborane
[1-bis(phenyl)-2-methylpent-4-enylsilylmethyl-1H-1,2,4-triazole]-diphenylvinylborane
[1-bis(phenyl)-3-methylpent-1-enylsilylmethyl-1H-1,2,4-triazole]-diphenylvinylborane
[1-bis(phenyl)-3-methylpent-2enylsilylmethyl-1H-1,2,4-triazole]-diphenylvinylborane
[1-bis(phenyl)-3-methylpent-3-enylsilylmethyl-1H-1,2,4-triazole]-diphenylvinylborane
[1-bis(phenyl)-4-methylpent-4-enylsilylmethyl-1H-1,2,4-triazole]-diphenylvinylborane

[1-bis(phenyl)-1-ethylbut-1-enylsilylmethyl-1H-1,2,4-triazole]-diphenylvinylborane
[1-bis(phenyl)-2-ethylbut-1-enylsilylmethyl-1H-1,2,4-triazole]-diphenylvinylborane
[1-bis(phenyl)-4-methylphenylsilylmethyl-1H-1,2,4-triazole]-diphenylvinylborane
[1-bis(phenyl)-4-ethylphenylsilylmethyl-1H-1,2,4-triazole]-diphenylvinylborane
[1-bis(phenyl)-4-propylphenylsilylmethyl-1H-1,2,4-triazole]-diphenylvinylborane
[1-bis(phenyl)-4-isopropylphenylsilylmethyl-1H-1,2,4-triazole]-diphenylvinylborane
[1-bis(phenyl)-4-n-butylphenylsilylmethyl-1H-1,2,4-triazole]-diphenylvinylborane
[1-bis(phenyl)-4-isobutylphenylsilylmethyl-1H-1,2,4-triazole]-diphenylvinylborane
[1-bis(phenyl)-4-t-butylphenylsilylmethyl-1H-1,2,4-triazole]-diphenylvinylborane
[1-bis(phenyl)-4-n-pentylphenylsilylmethyl-1H-1,2,4-triazole]-diphenylvinylborane
[1-bis(phenyl)-4-hexylphenylsilylmethyl-1H-1,2,4-triazole]-diphenylvinylborane
[1-bis(phenyl)-4-chlorophenylsilylmethyl-1H-1,2,4-triazole]-diphenylvinylborane
[1-bis(phenyl)-4-fluorophenylsilylmethyl-1H-1,2,4-triazole]-diphenylvinylborane
[1-bis(phenyl)-4-methoxyphenylsilylmethyl-1H-1,2,4-triazole]-diphenylvinylborane
[1-bis(phenyl)-4-ethoxyphenylsilylmethyl-1H-1,2,4-triazole]-diphenylvinylborane
[1-bis(phenyl)-4-propoxyphenylsilylmethyl-1H-1,2,4-triazole]-diphenylvinylborane
[1-bis(phenyl)-4-butoxyphenylsilylmethyl-1H-1,2,4-triazole]-diphenylvinylborane
[1-bis(phenyl)-4-pentoxyphenylsilylmethyl-1H-1,2,4-triazole]-diphenylvinylborane
[1-bis(phenyl)-4-hexoxyphenylsilylmethyl-1H-1,2,4-triazole]-diphenylvinylborane
[1-bis(phenyl)-4-thiomethylphenylsilylmethyl-1H-1,2,4-triazole]-diphenylvinylborane
[1-bis(phenyl)-4-thioethylphenylsilylmethyl-1H-1,2,4-triazole]-diphenylvinylborane
[1-bis(phenyl)-4-thiopropylphenylsilylmethyl-1H-1,2,4-triazole]-diphenylvinylborane
[1-bis(phenyl)-3-methylphenylsilylmethyl-1H-1,2,4-triazole]-diphenylvinylborane
[1-bis(phenyl)-3-ethylphenylsilylmethyl-1H-1,2,4-triazole]-diphenylvinylborane
[1-bis(phenyl)-3-propylphenylsilylmethyl-1H-1,2,4-triazole]-diphenylvinylborane
[1-bis(phenyl)-3-isopropylphenylsilylmethyl-1H-1,2,4-triazole]-diphenylvinylborane
[1-bis(phenyl)-3-n-butylphenylsilylmethyl-1H-1,2,4-triazole]-diphenylvinylborane
[1-bis(phenyl)-3-isobutylphenylsilylmethyl-1H-1,2,4-triazole]-diphenylvinylborane
[1-bis(phenyl)-3-t-butylphenylsilylmethyl-1H-1,2,4-triazole]-diphenylvinylborane
[1-bis(phenyl)-3-n-pentylphenylsilylmethyl-1H-1,2,4-triazole]-diphenylvinylborane
[1-bis(phenyl)-3-hexylphenylsilylmethyl-1H-1,2,4-triazole]-diphenylvinylborane
[1-bis(phenyl)-3-chlorophenylsilylmethyl-1H-1,2,4-triazole]-diphenylvinylborane
[1-bis(phenyl)-3-fluorophenylsilylmethyl-1H-1,2,4-triazole]-diphenylvinylborane
[1-bis(phenyl)-3-methoxyphenylsilylmethyl-1H-1,2,4-triazole]-diphenylvinylborane
[1-bis(phenyl)-3-ethoxyphenylsilylmethyl-1H-1,2,4-triazole]-diphenylvinylborane
[1-bis(phenyl)-3-propoxyphenylsilylmethyl-1H-1,2,4-triazole]-diphenylvinylborane
[1-bis(phenyl)-3-butoxyphenylsilylmethyl-1H-1,2,4-triazole]-diphenylvinylborane
[1-bis(phenyl)-3-pentoxyphenylsilylmethyl-1H-1,2,4-triazole]-diphenylvinylborane
[1-bis(phenyl)-3-hexoxyphenylsilylmethyl-1H-1,2,4-triazole]-diphenylvinylborane
[1-bis(phenyl)-3-thiomethylphenylsilylmethyl-1H-1,2,4--triazole]-diphenylvinylborane
[1-bis(phenyl)-3-thioethylphenylsilylmethyl-1H-1,2,4-triazole]-diphenylvinylborane
[1-bis(phenyl)-3-thiopropylphenylsilylmethyl-1H-1,2,4-triazole]-diphenylvinylborane
[1-triphenylsilylmethyl-1H-1,2,4-triazole]-diphenylcyclopropylborane
[1-bis(phenyl)methylsilylmethyl-1H-1,2,4-triazole]-diphenylcyclopropylborane
[1-bis(phenyl)ethylsilylmethyl-1H-1,2,4-triazole]-diphenylcyclopropylborane
[1-bis(phenyl)-n-propylsilylmethyl-1H-1,2,4-triazolediphenylcyclopropylborane
[1-bis(phenyl)-i-propylsilylmethyl-1H-1,2,4-triazole]-diphenylcyclopropylborane
[1-bis(phenyl)-n-butylsilylmethyl-1H-1,2,4-triazole]-diphenylcyclopropylborane
[1-bis(phenyl)-i-butylsilylmethyl-1H-1,2,4-triazole]-diphenylcyclopropylborane
[1-bis(phenyl)-t-butylsilylmethyl-1H-1,2,4-triazole]-diphenylcyclopropylborane
[1-bis(phenyl)cyclopropylsilylmethyl-1H-1 2,4-triazole]-diphenylcyclopropylborane
[1-bis(phenyl)cylcobutylsilylmethyl-1H-1,2,4-triazole]-diphenylcyclopropylborane
[1-bis(phenyl)cyclopentylsilylmethyl-1H-1,2,4-triazole]-diphenylcyclopropylborane
[1-bis(phenyl)cyclohexylsilylmethyl-1H-1,2,4-triazole]-diphenylcyclopropylborane
[1-bis(phenyl)vinylsilylmethyl-1H-1,2,4-triazole]-diphenylcyclopropylborane
[1-bis(phenyl)-1-propenylsilylmethyl-1H-1,2,4-triazole]-diphenylcyclopropylborane
[1-bis(phenyl)-2-propenylsilylmethyl-1H-1,2,4-triazole]-diphenylcyclopropylborane
[1-bis(phenyl)-1-methylvinylsilylmethyl-1H-1,2,4-triazole]-diphenylcyclopropylborane
[1-bis(phenyl)-1-butenylvinylsilylmethyl-1H-1,2,4-triazole]-diphenylcyclopropylborane
[1-bis(phenyl)-1-methylprop-1-enylsilylmethyl-1H-1,2,4-triazole]-diphenylcyclopropylborane
[1-bis(phenyl)-2-methylprop-1-enylsilylmethyl-1H-1,2,4-triazole]-diphenylcyclopropylborane
[1-bis(phenyl)-1-methylprop-2-enylsilylmethyl-1H-1,2,4-triazole]-diphenylcyclopropylborane
[1-bis(phenyl)-2-methylprop-2-enylsilylmethyl-1H-1,2,4-.-triazole]-diphenylcyclopropylborane
[1-bis(phenyl)-2-butenylsilylmethyl-1H-1,2,4-triazole]-diphenylcyclopropylborane
[1-bis(phenyl)-3-butenylsilylmethyl-1H-1,2,4-triazole]-diphenylcyclopropylborane
[1-bis(phenyl)-1-pentenylsilylmethyl-1H-1,2,4-triazole]-diphenylcyclopropylborane
[1-bis(phenyl)-2-pentenylsilylmethyl-1H-1,2,4-triazole]-diphenylcyclopropylborane
[1-bis(phenyl)-3-pentenylsilylmethyl-1H-1,2,4-triazole]-diphenylcyclopropylborane

[1-bis(phenyl)-4-pentenylsilylmethyl-1H-1,2,4-triazole]-diphenylcyclopropylborane
[1-bis(phenyl)-2-methylbut-2-enylsilylmethyl-1H-1,2,4-triazole]-diphenylcyclopropylborane
[1-bis(phenyl)-2-methylbut-3-enylsilylmethyl-1H-1,2,4-triazole]-diphenylcyclopropylborane
[1-bis(phenyl)-3-methylbut-1-enylsilylmethyl-1H-1,2,4-triazole]-diphenylcyclopropylborane
[1-bis(phenyl)-3-methylbut-2-enylsilylmethyl-1H-1,2,4-triazole]-diphenylcyclopropylborane
[1-bis(phenyl)-3-methylbut-3-enylsilylmethyl-1H-1,2,4-triazole]-diphenylcyclopropylborane
[1-bis(phenyl)-1-hexenylsilylmethyl-1H-1,2,4-triazole]-diphenylcyclopropylborane
[1-bis(phenyl)-2-hexenylsilylmethyl-1H-1,2,4-triazole]-diphenylcyclopropylborane
[1-bis(phenyl)-3-hexenylsilylmethyl-1H-1,2,4-triazole]-diphenylcyclopropylborane
[1-bis(phenyl)-4-hexenylsilylmethyl-1H-1,2,4-triazole]-diphenylcyclopropylborane
[1-bis(phenyl)-5-hexenylsilylmethyl-1H-1,2,4-triazole]-diphenylcyclopropylborane
[1-bis(phenyl)-1-methylpent-1-enylsilylmethyl-1H-1,2,4-triazole]-diphenylcyclopropylborane
[1-bis(phenyl)-1-methylpent-2-enylsilylmethyl-1H-1,2,4-triazole]-diphenylcyclopropylborane
[1-bis(phenyl)-1-methylpent-3-enylsilylmethyl-1H-1,2,4-triazole]-diphenylcyclopropylborane
[1-bis(phenyl)-1-methylpent-4-enylsilylmethyl-1H-1,2,4-triazole]-diphenylcyclopropylborane
[1-bis(phenyl)-2-methylpent-1-enylsilylmethyl-1H-1,2,4-triazole]-diphenylcyclopropylborane
[1-bis(phenyl)-2-methylpent-2-enylsilylmethyl-1H-1,2,4-triazole]-diphenylcyclopropylborane
[1-bis(phenyl)-2-methylpent-3-enylsilylmethyl-1H-1,2,4-triazole]-diphenylcyclopropylborane
[1-bis(phenyl)-2-methylpent-4-enylsilylmethyl-1H-1,2,4-triazole]-diphenylcyclopropylborane
[1-bis(phenyl)-3-methylpent-1-enylsilylmethyl-1H-1,2,4-triazole]-diphenylcyclopropylborane
[1-bis(phenyl)-3-methylpent-2-enylsilylmethyl-1H-1,2,4-triazole]-diphenylcyclopropylborane
[1-bis(phenyl)-3-methylpent-3-enylsilylmethyl-1H-1,2,4-triazole]-diphenylcyclopropylborane
[1-bis(phenyl)-4-methylpent-4-enylsilylmethyl-1H-1,2,4-triazole]-diphenylcyclopropylborane
[1-bis(phenyl)-1-ethylbut-1-enylsilylmethyl-1H-1,2,4-triazole]-diphenylcyclopropylborane
[1-bis(phenyl)-2-ethylbut-1-enylsilylmethyl-1H-1,2,4-triazole]-diphenylcyclopropylborane
[1-bis(phenyl)-4-methylphenylsilylmethyl-1H-1,2,4-triazole]-diphenylcyclopropylborane
[1-bis(phenyl) 4-ethylphenylsilylmethyl-1H-1,2,4-triazole]-diphenylcyclopropylborane
[1-bis(phenyl)-4-propylphenylsilylmethyl-1H-1,2,4-triazole]-diphenylcyclopropylborane
[1-bis(phenyl)-4-isopropylphenylsilylmethyl-1H-1,2,4-triazole]-diphenylcyclopropylborane
[1-bis(phenyl)-4-n-butylphenylsilylmethyl-1H-1,2,4-triazole]-diphenylcyclopropylborane
[1-bis(phenyl)-4-isobutylphenylsilylmethyl-1H-1,2,4-triazole]-diphenylcyclopropylborane
[1-bis(phenyl)-4-t-butylphenylsilylmethyl-1H-1,2,4-triazole]-diphenylcyclopropylborane
[1-bis(phenyl)-4-n-pentylphenylsilylmethyl-1H-1,2,4-triazole]-diphenylcyclopropylborane
[1-bis(phenyl)-4-hexylphenylsilylmethyl-1H-1,2,4-triazole]-diphenylcyclopropylborane
[1-bis(phenyl)-4-chlorophenylsilylmethyl-1H-1,2,4-triazole]-diphenylcyclopropylborane
[1-bis(phenyl)-4-fluorophenylsilylmethyl-1H-1,2,4-triazole]-diphenylcyclopropylborane
[1-bis(phenyl)-4-methoxyphenylsilylmethyl-1H-1,2,4-triazole]-diphenylcyclopropylborane
[1-bis(phenyl)-4-ethoxyphenylsilylmethyl-1H-1,2,4-triazole]-diphenylcyclopropylborane
[1-bis(phenyl)-4-propoxyphenylsilylmethyl-1H-1,2,4-triazole]-diphenylcyclopropylborane
[1-bis(phenyl)-4-butoxyphenylsilylmethyl-1H-1,2,4-triazole]-diphenylcyclopropylborane
[1-bis(phenyl)-4-pentoxyphenylsilylmethyl-1H-1,2,4-triazole]-diphenylcyclopropylborane
[1-bis(phenyl)-4-hexoxyphenylsilylmethyl-1H-1,2,4-triazole]-diphenylcyclopropylborane
[1-bis(phenyl)-4-thiomethylphenylsilylmethyl-1H-1,2,4-triazole]-diphenylcyclopropylborane
[1-bis(phenyl)-4-thioethylphenylsilylmethyl-1H-1,2,4-triazole]-diphenylcyclopropylborane
[1-bis(phenyl)-4-thiopropylphenylsilylmethyl-1H-1,2,4-triazole]-diphenylcyclopropylborane
[1-bis(phenyl)-3-methylphenylsilylmethyl-1H-1,2,4-triazole]-diphenylcyclopropylborane
[1-bis(phenyl)-3-ethylphenylsilylmethyl-1H-1,2,4-triazole]-diphenylcyclopropylborane
[1-bis(phenyl)-3-propylphenylsilylmethyl-1H-1,2,4-triazole]-diphenylcyclopropylborane
[1-bis(phenyl)-3-isopropylphenylsilylmethyl-1H-1,2,4-triazole]-diphenylcyclopropylborane
[1-bis(phenyl)-3-n-butylphenylsilylmethyl-1H-1,2,4-triazole]-diphenylcyclopropylborane
[1-bis(phenyl)-3-isobutylphenylsilylmethyl-1H-1,2,4-triazole]-diphenylcyclopropylborane
[1-bis(phenyl)-3-t-butylphenylsilylmethyl-1H-1,2,4-triazole]-diphenylcyclopropylborane
[1-bis(phenyl)-3-n-pentylphenylsilylmethyl-1H-1,2,4-triazole]-diphenylcyclopropylborane
[1-bis(phenyl)-3-hexylphenylsilylmethyl-1H-1,2,4-triazole]-diphenylcyclopropylborane
[1-bis(phenyl)-3-chlorophenylsilylmethyl-1H-1,2,4-triazole]-diphenylcyclopropylborane
[1-bis(phenyl)-3-fluorophenylsilylmethyl-1H-1,2,4-triazole]-diphenylcyclopropylborane
[1-bis(phenyl)-3-methoxyphenylsilylmethyl-1H-1,2,4-triazole]-diphenylcyclopropylborane
[1-bis(phenyl)-3-ethoxyphenylsilylmethyl-1H-1,2,4-triazole]-diphenylcyclopropylborane
[1-bis(phenyl)-3-propoxyphenylsilylmethyl-1H-1,2,4-triazole]-diphenylcyclopropylborane
[1-bis(phenyl)-3-butoxyphenylsilylmethyl-1H-1,2,4-triazole]-diphenylcyclopropylborane
[1-bis(phenyl)-3-pentoxyphenylsilylmethyl-1H-1,2,4-triazole]-diphenylcyclopropylborane
[1-bis(phenyl)-3-hexoxyphenylsilylmethyl-1H-1,2,4-triazole]-diphenylcyclopropylborane
[1-bis(phenyl)-3-thiomethylphenylsilylmethyl-1H-1,2,4-triazole]-diphenylcyclopropylborane
[1-bis(phenyl)-3-thioethylphenylsilylmethyl-1H-1,2,4-triazole]-diphenylcyclopropylborane
[1-bis(phenyl)-3-thiopropylphenylsilylmethyl-1H-1,2,4-triazole]-diphenylcyclopropylborane
[1-bis(4-methylphenyl)phenylsilylmethyl-1H-1,2,4-triazole]-diphenylmethylborane
[1-bis(4-ethylphenyl)phenylsilylmethyl-1H-1,2,4-triazole]-diphenylmethylborane
[1-bis(4-propylphenyl)phenylsilylmethyl-1H-1,2,4-triazole]-diphenylmethylborane

[1-bis(4-isopropylphenyl)phenylsilylmethyl-1H-1,2,4-triazole]-diphenylmethylborane
[1-bis(4-n-butylphenyl)phenylsilylmethyl-1H-1,2,4-triazole]-diphenylmethylborane
[1-bis(4-isobutylphenyl)phenylsilylmethyl-1H-1,2,4-triazole]-diphenylmethylborane
[1-bis(4-t-butylphenyl)phenylsilylmethyl-1H-1,2,4-triazole]-diphenylmethylborane
[1-bis(4-n-pentylphenyl)phenylsilylmethyl-1H-1,2,4-triazole]-diphenylmethylborane
[1-bis(4-hexylphenyl)phenylsilylmethyl-1H-1,2,4-triazole]-diphenylmethylborane
[1-bis(4-chlorophenyl)phenylsilylmethyl-1H-1,2,4-triazole]-diphenylmethylborane
[1-bis(4-fluorophenyl)phenylsilylmethyl-1H-1,2,4-triazole]-diphenylmethylborane
[1-bis(4-methoxyphenyl)phenylsilylmethyl-1H-1,2,4-triazole]-diphenylmethylborane
[1-bis(4-ethoxyphenyl)phenylsilylmethyl-1H-1,2,4-triazole]-diphenylmethylborane
[1-bis(4-propoxyphenyl)phenylsilylmethyl-1H-1,2,4-triazole]-diphenylmethylborane
[1-bis(4-butoxyphenyl)phenylsilylmethyl-1H-1,2,4-triazole]-diphenylmethylborane
[1-bis(4-pentoxyphenyl)phenylsilylmethyl-1H-1,2,4-triazole]-diphenylmethylborane
[1-bis(4-hexoxyphenyl)phenylsilylmethyl-1H-1,2,4-triazole]-diphenylmethylborane
[1-bis(4-thiomethylphenyl)phenylsilylmethyl-1H-1,2,4-triazole]-diphenylmethylborane
[1-bis(4-thioethylphenyl)phenylsilylmethyl-1H-1,2,4-triazole]-diphenylmethylborane
[1-bis(4-thiopropylphenyl)phenylsilylmethyl-1H-1,2,4-triazole]-diphenylmethylborane
[1-bis(3-methylphenyl)phenylsilylmethyl-1H-1,2,4-triazole]-diphenylmethylborane
[1-bis(3-ethylphenyl)phenylsilylmethyl-1H-1,2,4-triazole]-diphenylmethylborane
[1-bis(3-propylphenyl)phenylsilylmethyl-1H-1,2,4-triazole]-diphenylmethylborane
[1-bis(3-isopropylphenyl)phenylsilylmethyl-1H-1,2,4-triazole]-diphenylmethylborane
[1-bis(3-n-butylphenyl)phenylsilylmethyl-1H-1,2,4-triazole]-diphenylmethylborane
[1-bis(3-isobutylphenyl)phenylsilylmethyl-1H-1,2,4-triazole]-diphenylmethylborane
[1-bis(3-t-butylphenyl)phenylsilylmethyl-1H-1,2,4-triazole]-diphenylmethylborane
[1-bis(3-n-pentylphenyl)phenylsilylmethyl-1H-1,2,4-triazole]-diphenylmethylborane
[1-bis(3-hexylphenyl)phenylsilylmethyl-1H-1,2,4-triazole]-diphenylmethylborane
[1-bis(3-chlorophenyl)phenylsilylmethyl-1H-1,2,4-triazole]-diphenylmethylborane
[1-bis(3-fluorophenyl)phenylsilylmethyl-1H-1,2,4-triazole]-diphenylmethylborane
[1-bis(3-methoxyphenyl)phenylsilylmethyl-1H-1,2,4-triazole]-diphenylmethylborane
[1-bis(3-ethoxyphenyl)phenylsilylmethyl-1H-1,2,4-triazole]-diphenylmethylborane
[1-bis(3-propoxyphenyl)phenylsilylmethyl-1H-1,2,4-triazole]-diphenylmethylborane
[1-bis(3-butoxyphenyl)phenylsilylmethyl-1H-1,2,4-triazole]-diphenylmethylborane
[1-bis(3-pentoxyphenyl)phenylsilylmethyl-1H-1,2,4-triazole]-diphenylmethylborane
[1-bis(3-hexoxyphenyl)phenylsilylmethyl-1H-1,2,4-triazole]-diphenylmethylborane
[1-bis(3-thiomethylphenyl)phenylsilylmethyl-1H-1,2,4-triazole]-diphenylmethylborane
[1-bis(3-thioethylphenyl)phenylsilylmethyl-1H-1,2,4-triazole]-diphenylmethylborane
[1-bis(3-thiopropylphenyl)phenylsilylmethyl-1H-1,2,4-triazole]-diphenylmethylborane

EXAMPLE 4

[1-Bis(4-fluorophenyl)methylsilyl-1H-1,2,4-triazole]-triphenylboron

The title compound can be prepared by adding, to a solution of 1.3 g of triphenyl boron in 85 mL of diethyl ether, 1.7 g of 1-bis(4-fluorophenyl)methylsilylmethyl-1H-1,2,4-triazole in 5 mL of diethyl ether. The resulting mixture is stirred overnight, and the reaction is then quenched with 20 mL of a 20% HCl solution. The resulting aqueous and organic layers are separated and the organic layer is washed with 15 mL portions of water, and dried over magnesium sulfate. After the solvent is removed, an off-white powder is obtained; recrystallization of a portion of this powder in ethanol Similarly, by applying the above procedure using the appropriate starting materials, the following compounds can be prepared:
[1-triphenylsilylmethyl-1H-1,2,4-triazole]-triphenylborane
[1-bis(phenyl)methylsilylmethyl-1H-1,2,4-triazole]-triphenylborane
[1-bis(phenyl)ethylsilylmethyl-1H-1,2,4-triazole]-triphenylborane
[1-bis(phenyl)-n-propylsilylmethyl-1H-1,2,4-triazole]-triphenylborane
[1-bis(phenyl)-i-propylsilylmethyl-1H-1,2,4-triazole]-triphenylborane
[1-bis(phenyl)-n-butylsilylmethyl-1H-1,2,4-triazole]-triphenylborane
[1-bis(phenyl)-i-butylsilylmethyl-1H-1,2,4-triazole]-triphenylborane
[1-bis(phenyl)-t-butylsilylmethyl-1H-1,2,4-triazole]-triphenylborane
[1-bis(phenyl)cyclopropylsilylmethyl-1H-1,2,4-triazole]-triphenylborane
[1-bis(phenyl)cylcobutylsilylmethyl-1H-1,2,4-triazole]-triphenylborane
[1-bis(phenyl)cyclopentylsilylmethyl-1H-1,2,4-triazole]-triphenylborane
[1-bis(phenyl)cyclohexylsilylmethyl-1H-1,2,4-triazole]-triphenylborane
[1-bis(phenyl)vinylsilylmethyl-1H-1,2,4-triazole]-triphenylborane
[1-bis(phenyl)-1-propenylsilylmethyl-1H-1,2,4-triazole]-triphenylborane
[1-bis(phenyl)-2-propenylsilylmethyl-1H-1,2,4-triazole]-triphenylborane
[1-bis(phenyl)-1-methylvinylsilylmethyl-1H-1,2,4-triazole]-triphenylborane
[1-bis(phenyl)-1-butenylvinylsilylmethyl-1H-1,2,4-triazole]triphenylborane
[1-bis(phenyl)-1-methylprop-1-enylsilylmethyl-1H-1,2,4-triazole]-triphenylborane
[1-bis(phenyl)-2-methylprop-1-enylsilylmethyl-1H-1,2,4-triazole]-triphenylborane
[1-bis(phenyl)-1-methylprop-2-enylsilylmethyl-1H-1,2,4-triazole]-triphenylborane
[1-bis(phenyl)-2-methylprop-2-enylsilylmethyl-1H-1,2,4-triazole]-triphenylborane

[1-bis(phenyl)-2-butenylsilylmethyl-1H-1,2,4-triazole]-triphenylborane
[1-bis(phenyl)-3-butenylsilylmethyl-1H-1,2,4-triazole]-triphenylborane
[1-bis(phenyl)-1-pentenylsilylmethyl-1H-1,2,4-triazole]-triphenylborane
[1-bis(phenyl)-2-pentenylsilylmethyl-1H-1,2,4-triazole]-triphenylborane
[1-bis(phenyl)-3-pentenylsilylmethyl-1H-1,2,4-triazole]-triphenylborane
[1-bis(phenyl)-4-pentenylsilylmethyl-1H-1,2,4-triazole]-triphenylborane
[1-bis(phenyl)-2-methylbut-2-enylsilylmethyl-1H-1,2,4-triazole]-triphenylborane
[1-bis(phenyl)-2-methylbut-3-enylsilylmethyl-1H-1,2,4-triazole]-triphenylborane
[1-bis(phenyl)-3-methylbut-1-enylsilylmethyl-1H-1,2,4-triazole]-triphenylborane
[1-bis(phenyl)-3-methylbut-2-enylsilylmethyl-1H-1,2,4-triazole]-triphenylborane
[1-bis(phenyl)-3-methylbut-3-enylsilylmethyl-1H-1,2,4-triazole]-triphenylborane
[1-bis(phenyl)-1-hexenylsilylmethyl-1H-1,2,4-triazole]-triphenylborane
[1-bis(phenyl)-2-hexenylsilylmethyl-1H-1,2,4-triazole]-triphenylborane
[1-bis(phenyl)-3-hexenylsilylmethyl-1H-1,2,4-triazole]-triphenylborane
[1-bis(phenyl)-4-hexenylsilylmethyl-1H-1,2,4-triazole]-triphenylborane
[1-bis(phenyl)-5-hexenylsilylmethyl-1H-1,2,4-triazole]-diphenylmethylborane
[1-bis(phenyl)-1-methylpent-1-enylsilylmethyl-1H-1,2,4-triazole]-triphenylborane
[1-bis(phenyl)-1-methylpent-2-enylsilylmethyl-1H-1,2,4-triazole]-triphenylborane
[1-bis(phenyl)-1-methylpent-3-enylsilylmethyl-1H-1,2,4-triazole]-triphenylborane
[1-bis(phenyl)-1-methylpent-4-enylsilylmethyl-1H-1,2,4-triazole]-triphenylborane
[1-bis(phenyl)-2-methylpent-1-enylsilylmethyl-1H-1,2,4-triazole]-triphenylborane
[1-bis(phenyl)-2-methylpent-2-enylsilylmethyl-1H-1,2,4-triazole]-triphenylborane
[1-bis(phenyl)-2-methylpent-3-enylsilylmethyl-1H-1,2,4-triazole]-triphenylborane
[1-bis(phenyl)-2-methylpent-4-enylsilylmethyl-1H-1,2,4-triazole]-triphenylborane
[1-bis(phenyl)-3-methylpent-1-enylsilylmethyl-1H-1,2,4-triazole]-triphenylborane
[1-bis(phenyl)-3-methylpent-2-enylsilylmethyl-1H-1,2,4-triazole]-triphenylborane
[1 henyl)-3-methylpent-3-enylsilylmethyl-1H-1,2,4-triazole]-triphenylborane
[1-bis(phenyl)-4-methylpent-4-enylsilylmethyl-1H-1,2,4-triazole]-triphenylborane
[1-bis(phenyl)-1-ethylbut-1-enylsilylmethyl-1H-1,2,4-triazole]-triphenylborane
[1-bis(phenyl)-2-ethylbut-1-enylsilylmethyl-1H-1,2,4-triazole]-triphenylborane
[1-bis(phenyl)-4-methylphenylsilylmethyl-1H-1,2,4-triazole]-triphenylborane
[1-bis(phenyl)-4-ethylphenylsilylmethyl-1H-1,2,4-triazole]-triphenylborane
[1-bis(phenyl)-4-propylphenylsilylmethyl-1H-1,2,4-triazole]-triphenylborane
[1-bis(phenyl)-4-isopropylphenylsilylmethyl-1H-1,2,4-triazole]-diphenylmethylborane
[1-bis(phenyl)-4-n-butylphenylsilylmethyl-1H-1,2,4-triazole]-triphenylborane
[1-bis(phenyl)-4-isobutylphenylsilylmethyl-1H-1,2,4-triazole]-triphenylborane
[1-bis(phenyl)-4-t-butylphenylsilylmethyl-1H-1,2,4-triazole]-triphenylborane
[1-bis(phenyl)-4-n-pentylphenylsilylmethyl-1H-1,2,4-triazole]-triphenylborane
[1-bis(phenyl)-4-hexylphenylsilylmethyl-1H-1,2,4-triazole]-triphenylborane
[1-bis(phenyl)-4-chlorophenylsilylmethyl-1H-1,2,4-triazole]-triphenylborane
[1-bis(phenyl)-4-fluorophenylsilylmethyl-1H-1,2,4-triazole]-triphenylborane
[1-bis(phenyl)-4-methoxyphenylsilylmethyl-1H-1,2,4-triazole]-triphenylborane
[1-bis(phenyl)-4-ethoxyphenylsilylmethyl-1H-1,2,4-triazole]-triphenylborane
[1-bis(phenyl)-4-propoxyphenylsilylmethyl-1H-1,2,4-triazole]-triphenylborane
[1-bis(phenyl)-4-butoxyphenylsilylmethyl-1H-1,2,4-triazole]-triphenylborane
[1-bis(phenyl)-4-pentoxyphenylsilylmethyl-1H-1,2,4-triazole]-triphenylborane
[1-bis(phenyl)-4-hexoxyphenylsilylmethyl-1H-1,2,4-triazole]-triphenylborane
[1-bis(phenyl)-4-thiomethylphenylsilylmethyl-1H-1,2,4-triazole]-triphenylborane
[1-bis(phenyl)-4-thioethylphenylsilylmethyl-1H-1,2,4-triazole]-triphenylborane
[1-bis(phenyl)-4-thiopropylphenylsilylmethyl-1H-1,2,4-triazole]-triphenylborane
[1-bis(phenyl)-3-methylphenylsilylmethyl-1H-1,2,4-triazole]-triphenylborane
[1-bis(phenyl)-3-ethylphenylsilylmethyl-1H-1,2,4-triazole]-diphenylmethylborane
[1-bis(phenyl)-3-propylphenylsilylmethyl-1H-1,2,4-triazole]-triphenylborane
[1-bis(phenyl)-3-isopropylphenylsilylmethyl-1H-1,2,4-triazole]-triphenylborane
[1-bis(phenyl)-3-n-butylphenylsilylmethyl-1H-1,2,4-triazole]-triphenylborane
[1-bis(phenyl)-3-isobutylphenylsilylmethyl-1H-1,2,4-triazole]-triphenylborane
[1-bis(phenyl)-3-t-butylphenylsilylmethyl-1H-1,2,4-triazole]-triphenylborane
[1-bis(phenyl)-3-n-pentylphenylsilylmethyl-1H-1,2,4-triazole]-triphenylborane
[1-bis(phenyl)-3-hexylphenylsilylmethyl-1H-1,2,4-triazole]-triphenylborane
[1-bis(phenyl)-3-chlorophenylsilylmethyl-1H-1,2,4-triazole]-triphenylborane
[1-bis(phenyl)-3-fluorophenylsilylmethyl-1H-1,2,4-triazole]-triphenylborane
[1-bis(phenyl)-3-methoxyphenylsilylmethyl-1H-1,2,4-triazole]-triphenylborane
[1-bis(phenyl)-3-ethoxyphenylsilylmethyl-1H-1,2,4-triazole]-triphenylborane
[1-bis(phenyl)-3-propoxyphenylsilylmethyl-1H-1,2,4-triazole]-triphenylborane
[1-bis(phenyl)-3-butoxyphenylsilylmethyl-1H-1,2,4-triazole]-triphenylborane
[1-bis(phenyl)-3-pentoxyphenylsilylmethyl-1H-1,2,4-triazole]-triphenylborane
[1-bis(phenyl)-3-hexoxyphenylsilylmethyl-1H-1,2,4-triazole]-triphenylborane
[1-bis(phenyl)-3-thiomethylphenylsilylmethyl-1H-1,2,4-triazole]-triphenylborane

[1-bis(phenyl)-3-thioethylphenylsilylmethyl-1H-1,2,4-triazole]-triphenylborane
[1-bis(phenyl)-3-thiopropylphenylsilylmethyl-1H-1,2,4-triazole]-diphenylmethylborane
[1-bis(4-methylphenyl)phenylsilylmethyl-1H-1,2,4-triazole]-triphenylborane
[1-bis(4-ethylphenyl)phenylsilylmethyl-1H-1,2,4-triazole]-triphenylborane
[1-bis(4-propylphenyl)phenylsilylmethyl-1H-1,2,4-triazole]-triphenylborane
[1-bis(4-isopropylphenyl)phenylsilylmethyl-1H-1,2,4-triazole]-triphenylborane
[1-bis(4-n-butylphenyl)phenylsilylmethyl-1H-1,2,4-triazole]-triphenylborane triazole]-triphenylborane
[1-bis(4-isobutylphenyl)phenylsilylmethyl-1H-1,2,4-triazole]-triphenylborane
[1-bis(4-t-butylphenyl)phenylsilylmethyl-1H-1,2,4-triazole]-triphenylborane
[1-bis(4-n-pentylphenyl)phenylsilylmethyl-1H-1,2,4-triazole]-triphenylborane
[1-bis(4-hexylphenyl)phenylsilylmethyl-1H-1,2,4-triazole]-triphenylborane
[1-bis(4-chlorophenyl)phenylsilylmethyl-1H-1,2,4-triazole]-triphenylborane
[1-bis(4-fluorophenyl)phenylsilylmethyl-1H-1,2,4-triazole]-triphenylborane
[1-bis(4-methoxyphenyl)phenylsilylmethyl-1H-1,2,4-triazole]-triphenylborane
[1-bis(4-ethoxyphenyl)phenylsilylmethyl-1H-1,2,4-triazole]-triphenylborane
[1-bis(4-propoxyphenyl)phenylsilylmethyl-1H-1,2,4-triazole]-triphenylborane
[1-bis(4-butoxyphenyl)phenylsilylmethyl-1H-1,2,4-triazole]-triphenylborane
[1-bis(4-pentoxyphenyl)phenylsilylmethyl-1H-1,2,4-triazole]-triphenylborane
[1-bis(4-hexoxyphenyl)phenylsilylmethyl-1H-1,2,4-triazole]-triphenylborane
[1-bis(4-thiomethylphenyl)phenylsilylmethyl-1H-1,2,4-triazole]-triphenylborane
[1-bis(4-thioethylphenyl)phenylsilylmethyl-1H-1,2,4-triazole]-triphenylborane
[1-bis(4-thiopropylphenyl)phenylsilylmethyl-1H-1,2,4-triazole]-triphenylborane
[1-bis(3-methylphenyl)phenylsilylmethyl-1H-1,2,4-triazole]-triphenylborane
[1-bis(3-ethylphenyl)phenylsilylmethyl-1H-1,2,4-triazole]-triphenylborane
[1-bis(3-propylphenyl)phenylsilylmethyl-1H-1,2,4-triazole]-triphenylborane
[1-bis(3-isopropylphenyl)phenylsilylmethyl-1H-1,2,4-triazole]-triphenylborane
[1-bis(3-n-butylphenyl)phenylsilylmethyl-1H-1,2,4-triazole]-triphenylborane
[1-bis(3-isobutylphenyl)phenylsilylmethyl-1H-1,2,4-triazole]-triphenylborane
[1-bis(3-t-butylphenyl)phenylsilylmethyl-1H-1,2,4-triazole]-triphenylborane
[1-bis(3-n-pentylphenyl)phenylsilylmethyl-1H-1,2,4-triazole]-triphenylborane
[1-bis(3-hexylphenyl)phenylsilylmethyl-1H-1,2,4-triazole]-triphenylborane
[1-bis(3-chlorophenyl)phenylsilylmethyl-1H-1,2,4-triazole]-triphenylborane
[1-bis(3-fluorophenyl)phenylsilylmethyl-1H-1,2,4-triazole]-triphenylborane
[1-bis(3-methoxyphenyl)phenylsilylmethyl-1H-1,2,4-triazole]-triphenylborane
[1-bis(3-ethoxyphenyl)phenylsilylmethyl-1H-1,2,4-triazole]-triphenylborane
[1-bis(3-propoxyphenyl)phenylsilylmethyl-1H-1,2,4-triazole]-triphenylborane
[1-bis(3-butoxyphenyl)phenylsilylmethyl-1H-1,2,4-triazole]-triphenylborane
[1-bis(3-pentoxyphenyl)phenylsilylmethyl-1H-1,2,4-triazole]-triphenylborane
[1-bis(3-hexoxyphenyl)phenylsilylmethyl-1H-1,2,4-triazole]-triphenylborane
[1-bis(3-thiomethylphenyl)phenylsilylmethyl-1H-1,2,4-triazole]-triphenylborane
[1-bis(3-thioethylphenyl)phenylsilylmethyl-1H-1,2,4-triazole]-triphenylborane
[1-bis(3-thiopropylphenyl)phenylsilylmethyl-1H-1,2,4-triazole]-triphenylborane

EXAMPLE 5

(1-[Bis(4-fluorophenyl)methylsilylmethyl]imidazole)-triphenylborane

The title compound can be prepared by adding 1.5 g of 1-[bis(4-fluorophenyl)methylsilylmethyl]imidazole to a solution of 1.1 g of triphenyl boron in 40 mL of diethyl ether. The resulting mixture is stirred at room temperature overnight, after which the reaction is quenched with 50 mL of a 1.5% solution of HCl and then extracted with three 50-mL portions of diethyl ether. The combined extract is washed with two 100-mL portions of brine and dried over magnesium sulfate. Removal of solvent by rotary evaporation yields a white solid with a melting point of 140°-141° C.

Similarly, by applying the above procedure using the appropriate starting materials, the following compounds can be prepared:
(1-[triphenylsilylmethyl]imidazole)-triphenylborane
(1-[bis(phenyl)methylsilylmethyl]imidazole)-triphenylborane
(1-[bis(phenyl)ethylsilylmethyl]imidazole)-triphenylborane
(1-[bis(phenyl)-n-propylsilylmethyl]imidazole)-triphenylborane
(1-[bis(phenyl)-i-propylsilylmethyl]imidazole)-triphenylborane
(1-[bis(phenyl)-n-butylsilylmethyl]imidazole)-triphenylborane
(1-[bis(phenyl)-i-butylsilylmethyl]imidazole)-triphenylborane
(1-[bis(phenyl)-t-butylsilylmethyl]imidazole)-triphenylborane
(1-[bis(phenyl)cyclopropylsilylmethyl]imidazole)-triphenylborane
(1-[bis(phenyl)cylcobutylsilylmethyl]imidazole)-triphenylborane
(1-[bis(phenyl)cyclopentylsilylmethyl]imidazole)-triphenylborane
(1-[bis(phenyl)cyclohexylsilylmethyl]imidazole)-triphenylborane
(1-[bis(phenyl)vinylsilylmethyl]imidazole)-triphenylborane
(1-[bis(phenyl)-1-propenylsilylmethyl]imidazole)-triphenylborane
(1-[bis(phenyl)-2-propenylsilylmethyl]imidazole)-triphenylborane
(1-[bis(phenyl)-1-methylvinylsilylmethyl]imidazole)-triphenylborane
(1-[bis(phenyl)-1-butenylvinylsilylmethyl]imidazole)-triphenylborane (1-[bis(phenyl)-1-methylprop-1-enylsilylmethyl]imidazole)-triphenylborane
(1-[bis(phenyl)-2-methylprop-1-enylsilylmethyl]imidazole)-triphenylborane
(1-[bis(phenyl)-1-methylprop-2-enylsilylmethyl]imidazole)-triphenylborane
(1-[bis(phenyl)-2-methylprop-2-enylsilylmethyl]imidazole)-triphenylborane
(1-[bis(phenyl)-2-butenylsilylmethyl]imidazole)-triphenylborane
(1-[bis(phenyl)-3-butenylsilylmethyl]imidazole)-triphenylborane
(1-[bis(phenyl)-1-pentenylsilylmethyl]imidazole)-triphenylborane
(1-[bis(phenyl)-2-pentenylsilylmethyl]imidazole)-triphenylborane
(1-[bis(phenyl)-3-pentenylsilylmethyl]imidazole)-triphenylborane
(1-[bis(phenyl)-4-pentenylsilylmethyl]imidazole)-triphenylborane
(1-[bis(phenyl)-2-methylbut-2-enylsilylmethyl]imidazole)-triphenylborane
(1-[bis(phenyl)-2-methylbut-3-enylsilylmethyl]imidazole)-triphenylborane
(1-[bis(phenyl)-3-methylbut-1-enylsilylmethyl]imidazole)-triphenylborane
(1-[bis(phenyl)-3-methylbut-2-enylsilylmethyl]imidazole)-triphenylborane
(1-[bis(phenyl)-3-methylbut-3-enylsilylmethyl]imidazole)-triphenylborane
(1-[bis(phenyl)-1-hexenylsilylmethyl]imidazole)-triphenylborane
(1-[bis(phenyl)-2-hexenylsilylmethyl]imidazole)-triphenylborane
(1-[bis(phenyl)-3-hexenylsilylmethyl]imidazole)-triphenylborane
(1-[bis(phenyl)-4-hexenylsilylmethyl]imidazole)-triphenylborane
(1-[bis(phenyl)-5-hexenylsilylmethyl]imidazole)-triphenylborane
(1-[bis(phenyl)-1-methylpent-1-enylsilylmethyl]imidazole)-triphenylborane
(1-[bis(phenyl)-1-methylpent-2-enylsilylmethyl]imidazole)-triphenylborane
(1-[bis(phenyl)-1-methylpent-3-enylsilylmethyl]imidazole)-triphenylborane
(1-[bis(phenyl)-1-methylpent-4-enylsilylmethyl]imidazole)-triphenylborane
(1-[bis(phenyl)-2-methylpent-1-enylsilylmethyl]imidazole)-triphenylborane
(1-[bis(phenyl)-2-methylpent-2-enylsilylmethyl]imidazole)-triphenylborane
(1-[bis(phenyl)-2-methylpent-3-enylsilylmethyl]imidazole)-triphenylborane
(1-[bis(phenyl)-2-methylpent-4-enylsilylmethyl]imidazole)-triphenylborane
(1-[bis(phenyl)-3-methylpent-1-enylsilylmethyl]imidazole)-triphenylborane
(1-[bis(phenyl)-3-methylpent-2-enylsilylmethyl]imidazole)-triphenylborane
(1-[bis(phenyl)-3-methylpent-3-enylsilylmethyl]imidazole)-triphenylborane
(1-[bis(phenyl)-4-methylpent-4-enylsilylmethyl]imidazole)-triphenylborane
(1-[bis(phenyl)-1-ethylbut-1-enylsilylmethyl]imidazole)-triphenylborane
(1-[bis(phenyl)-2-ethylbut-1-enylsilylmethyl]imidazole)-triphenylborane
(1-[bis(phenyl)-4-methylphenylsilylmethyl]imidazole)-triphenylborane
(1-[bis(phenyl)-4-ethylphenylsilylmethyl]imidazole)-triphenylborane
(1-[bis(phenyl)-4-propylphenylsilylmethyl]imidazole)-triphenylborane
(1-[bis(phenyl)-4-isopropylphenylsilylmethyl]imidazole)-triphenylborane
(1-[bis(phenyl)-4-n-butylphenylsilylmethyl]imidazole)-triphenylborane
(1-[bis(phenyl)-4-isobutylphenylsilylmethyl]imidazole)-triphenylborane
(1-[bis(phenyl)-4-t-butylphenylsilylmethyl]imidazole)-triphenylborane
(1-[bis(phenyl)-4-n-pentylphenylsilylmethyl]imidazole)-triphenylborane
(1-[bis(phenyl)-4-hexylphenylsilylmethyl]imidazole)-triphenylborane
(1-[bis(phenyl)-4-chlorophenylsilylmethyl]imidazole)-triphenylborane
(1-[bis(phenyl)-4-fluorophenylsilylmethyl]imidazole)-triphenylborane
(1-[bis(phenyl)-4-methoxyphenylsilylmethyl]imidazole)-triphenylborane
(1-[bis(phenyl)-4-ethoxyphenylsilylmethyl]imidazole)-triphenylborane
(1-[bis(phenyl)-4-propoxyphenylsilylmethyl]imidazole)-triphenylborane
(1-[bis(phenyl)-4-butoxyphenylsilylmethyl]imidazole)-triphenylborane
(1-[bis(phenyl)-4-pentoxyphenylsilylmethyl]imidazole)-triphenylborane
(1-[bis(phenyl)-4-hexoxyphenylsilylmethyl]imidazole)-triphenylborane
(1-[bis(phenyl)-4-thiomethylphenylsilylmethyl]imidazole)-triphenylborane
(1-[bis(phenyl)-4-thioethylphenylsilylmethyl]imidazole)-triphenylborane
(1-[bis(phenyl)-4-thiopropylphenylsilylmethyl]imidazole)-triphenylborane
(1-[bis(phenyl)-3-methylphenylsilylmethyl]imidazole)-triphenylborane
(1-[bis(phenyl)-3-ethylphenylsilylmethyl]imidazole)-triphenylborane
(1-[bis(phenyl)-3-propylphenylsilylmethyl]imidazole)-triphenylborane
(1-[bis(phenyl)-3-isopropylphenylsilylmethyl]imidazole)-triphenylborane
(1-[bis(phenyl)-3-n-butylphenylsilylmethyl]imidazole)-triphenylborane
(1-[bis(phenyl)-3-isobutylphenylsilylmethyl]imidazole)-triphenylborane
(1-[bis(phenyl)-3-t-butylphenylsilylmethyl]imidazole)-triphenylborane
(1-[bis(phenyl)-3-n-pentylphenylsilylmethyl]imidazole)-triphenylborane
(1-[bis(phenyl)-3-hexylphenylsilylmethyl]imidazole)-triphenylborane
(1-[bis(phenyl)-3-chlorophenylsilylmethyl]imidazole)-triphenylborane
(1-[bis(phenyl)-3-fluorophenylsilylmethyl]imidazole)-triphenylborane
(1-[bis(phenyl)-3-methoxyphenylsilylmethyl]imidazole)-triphenylborane
(1-[bis(phenyl)-3-ethoxyphenylsilylmethyl]imidazole)-triphenylborane
(1-[bis(phenyl)-3-propoxyphenylsilylmethyl]imidazole)-triphenylborane (1-[bis(phenyl)-3-butoxyphenylsilylmethyl]imidazole)-triphenylborane
(1-[bis(phenyl)-3-pentoxyphenylsilylmethyl]imidazole)-triphenylborane
(1-[bis(phenyl)-3-hexoxyphenylsilylmethyl]imidazole)-triphenylborane
(1-[bis(phenyl)-3-thiomethylphenylsilylmethyl]imidazole)-triphenylborane
(1-[bis(phenyl)-3-thioethylphenylsilylmethyl]imidazole)-triphenylborane
(1-[bis(phenyl)-3-thiopropylphenylsilylmethyl]imidazole)-triphenylborane
(1-[bis(4-methylphenyl)phenylsilylmethyl]imidazole)-triphenylborane
(1-[bis(4-ethylphenyl)phenylsilylmethyl]imidazole)-triphenylborane
(1-[bis(4-propylphenyl)phenylsilylmethyl]imidazole)-triphenylborane
(1-[bis(4-isopropylphenyl)phenylsilylmethyl]imidazole)-triphenylborane
(1-[bis(4-n-butylphenyl)phenylsilylmethyl]imidazole)-triphenylborane
(1-[bis(4-isobutylphenyl)phenylsilylmethyl]imidazole)-triphenylborane
(1-[bis(4-t-butylphenyl)phenylsilylmethyl]imidazole)-triphenylborane
(1-[bis(4-n-pentylphenyl)phenylsilylmethyl]imidazole)-triphenylborane
(1-[bis(4-hexylphenyl)phenylsilylmethyl]imidazole)-triphenylborane
(1-[bis(4-chlorophenyl)phenylsilylmethyl]imidazole)-triphenylborane
(1-[bis(4-fluorophenyl)phenylsilylmethyl]imidazole)-triphenylborane
(1-[bis(4-methoxyphenyl)phenylsilylmethyl]imidazole)-triphenylborane
(1-[bis(4-ethoxyphenyl)phenylsilylmethyl]imidazole)-triphenylborane
(1-[bis(4-propoxyphenyl)phenylsilylmethyl]imidazole)-triphenylborane
(1-[bis(4-butoxyphenyl)phenylsilylmethyl]imidazole)-triphenylborane
(1-[bis(4-pentoxyphenyl)phenylsilylmethyl]imidazole)-triphenylborane
(1-[bis(4-hexoxyphenyl)phenylsilylmethyl]imidazole)-triphenylborane
(1-[bis(4-thiomethylphenyl)phenylsilylmethyl]imidazole)-triphenylborane
(1-[bis(4-thioethylphenyl)phenylsilylmethyl]imidazole)-triphenylborane
(1-[bis(4-thiopropylphenyl)phenylsilylmethyl]imidazole)-triphenylborane
(1-[bis(3-methylphenyl)phenylsilylmethyl]imidazole)-triphenylborane
(1-[bis(3-ethylphenyl)phenylsilylmethyl]imidazole)-triphenylborane
(1-[bis(3-propylphenyl)phenylsilylmethyl]imidazole)-triphenylborane
(1-[bis(3-isopropylphenyl)phenylsilylmethyl]imidazole)-triphenylborane
(1-[bis(3-n-butylphenyl)phenylsilylmethyl]imidazole)-triphenylborane
(1-[bis(3-isobutylphenyl)phenylsilylmethyl]imidazole)-triphenylborane
(1-[bis(3-t-butylphenyl)phenylsilylmethyl]imidazole)-triphenylborane
(1-[bis(3-n-pentylphenyl)phenylsilylmethyl]imidazole)-triphenylborane
(1-[bis(3-hexylphenyl)phenylsilylmethyl]imidazole)-triphenylborane
(1-[bis(3-chlorophenyl)phenylsilylmethyl]imidazole)-triphenylborane
(1-[bis(3-fluorophenyl)phenylsilylmethyl]imidazole)-triphenylborane
(1-[bis(3-methoxyphenyl)phenylsilylmethyl]imidazole)-triphenylborane
(1-[bis(3-ethoxyphenyl)phenylsilylmethyl]imidazole)-triphenylborane
(1-[bis(3-propoxyphenyl)phenylsilylmethyl]imidazole)-triphenylborane
(1-[bis(3-butoxyphenyl)phenylsilylmethyl]imidazole)-triphenylborane
(1-[bis(3-pentoxyphenyl)phenylsilylmethyl]imidazole)-triphenylborane
(1-[bis(3-hexoxyphenyl)phenylsilylmethyl]imidazole)-triphenylborane
(1-[bis(3-thiomethylphenyl)phenylsilylmethyl]imidazole)-triphenylborane
(1-[bis(3-thioethylphenyl)phenylsilylmethyl]imidazole)-triphenylborane
(1-[bis(3-thiopropylphenyl)phenylsilylmethyl]imidazole)-triphenylborane

EXAMPLE 6

Similarly, by applying the same general procedures described in the appropriate Examples set forth above using the appropriate starting materials, the compounds identified in Table A below were prepared:

TABLE A

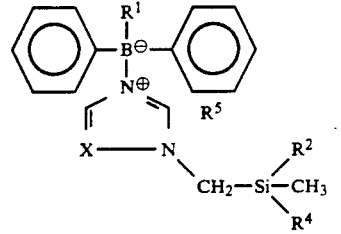

| No. | $R^1$ | X | $R^2 = R^4$ | m.p. (°C.) |
|---|---|---|---|---|
| 1 | vinyl | CH | 4-fluorophenyl | 126–127 |
| 2 | methyl | CH | phenyl | 123–124 |
| 3 | vinyl | CH | phenyl | 100–102 |
| 4 | methyl | CH | 4-methylphenyl | 124–125 |
| 5 | methyl | CH | 4-chlorophenyl | 130–132 |
| 6 | cyclopropyl | CH | 4-fluorophenyl | 108–109 |
| 7 | vinyl | CH | trifluoromethyl | 142–143 |
| 8 | vinyl | CH | methyl | 135–143 |
| 9 | vinyl | N | 4-fluorophenyl | 111–112 |
| 10 | vinyl | N | phenyl | 105–106 |
| 11 | methyl | N | 4-fluorophenyl | 111–112 |
| 12 | methyl | N | methyl | 124–125 |
| 13 | methyl | N | 4-methylphenyl | 121–123 |
| 14 | vinyl | N | 4-methylphenyl | 113–115 |
| 15 | methyl | N | 4-chlorophenyl | 121–123 |
| 16 | vinyl | N | 4-chlorophenyl | 115–116 |
| 17 | phenyl | N | 4-methylphenyl | 130–132 |
| 18 | phenyl | N | 4-chlorophenyl | 82–90 |
| 19 | phenyl | N | 4-fluorophenyl | 135–137 |
| 20 | phenyl | N | phenyl | 148–150 |
| 21 | phenyl | CH | 4-fluorophenyl | 140–141 |
| 22 | phenyl | CH | phenyl | 161–162 |
| 23 | phenyl | CH | 4-chlorophenyl | 171–172 |
| 24 | phenyl | CH | methyl | 156–158 |

EXAMPLE 7

The compounds identified in Table A hereinabove were tested for the preventative control of certain plant diseases by the procedures described below. The results of this testing are set forth in Table 1 hereinbelow, wherein Compound Numbers refer to the Compound Numbers assigned the respective compounds in Tables A.

Tomato Late Blight (TLB)

Compounds of the invention were tested for the preventative control of the Tomato Late Blight organism *Phytophthora infestans*. Three to six week old tomato (cultivar Bonny Best) seedlings were used. The tomato plants were sprayed with either a 500 or 200 ppm suspension of the test compound in acetone, water and a non-ionic emulsifier. The sprayed plants were then inoculated 1 day later with the organism, placed in an environmental chamber and incubated at 66° F. to 68° F. and 100% relative humidity for 16 to 24 hours. Following the incubation, the plants were maintained in a greenhouse for approximately 7 days. The percent disease control provided by a given test compound was based on the percent disease reduction relative to untreated check plants.

The averaged results are reported in Table 1.

Rice Blast (RB)

Compounds of this invention were tested for control of the Rice Blast organism *Piricularia oryzae*, using 10 to 14 day old rice plant seedlings (Calrose M-9 variety). Seedling plants were sprayed with a 500 or 200 ppm solution of the test compound in acetone, water and a non-ionic emulsifier. The sprayed plants were inoculated 1 day later with the organism in an environmental chamber. After inoculation, the plants were kept in an environmental chamber for about 48 hours under conditions of about 72° F. to 75° F. and about 100% relative humidity. Following the incubation period, the plants were placed in a greenhouse with a temperature of about 80° F. and maintained with bottom watering for about 12 to 16 days. The percent disease control provided by a given test compound is based on a comparison of the percentage disease relative to the percent disease development on untreated check plants.

The averaged results are reported in Table 1.

Celery Late Blight (CLB)

The Celery Late Blight tests were conducted using celery (Utah) plants 11 weeks old. The Celery Late Blight organism was *Septoria apii*. The celery plants were sprayed with either 500 or 200 ppm solutions of the test compound mixed with acetone, water and a non-ionic emulsifier. The plants were then inoculated one day later with the organism and placed in an environmental chamber and incubated at 66° F. to 68° F. in 100% relative humidity for approximately 48 hours. Following the incubation, the plants were allowed to dry and then were maintained in a greenhouse for approximately 14 days. One plant was used per compound. Six untreated plants were used as the check for each screening group of compound The percent disease control provided by a given candidate toxicant is based on the percent disease reduction relative to untreated check plants.

The results are reported in Table 1.

Bean Powdery Mildew (BPM)

The compounds of the invention were tested for the control of the Bean Powdery Mildew organism, *Erysiphe polygoni*. Seedling bean plants were sprayed with a 500 or 200 ppm solution of the test compound in acetone, water and a nonionic emulsifier. The sprayed plants were then inoculated 1 day later with the organism. The plants were maintained for 10 days at temperatures of 68° F. at night with daytime temperatures of 72° F. to 80° F.; relative humidity was maintained at 40% to 60%. One plant was used per compound Six untreated plants were used as the check for each screening group of compounds. The percent disease control provided by a given test compound was based on the percent disease reduction relative to the untreated check plants The results are reported in Table 1.

Bean Rust (BR)

The Leaf Rust test was made using pinto beans. The pathogen was *Uromyces phaseoli tipica*. The bean plants were sprayed with either a 500 or 200 ppm solution of the test compound in an acetone-water mixture containing a nonionic emulsifier. The treated plants were inoculated thereafter with the pathogen and then incubated in an environmental chamber for approximately 20 hours at 100% relative humidity and a temperature of 68° F. to 70° F. The plants were then removed from the chamber, allowed to dry, and then maintained in a greenhouse at a 60% to 80% relative humidity. The amount of infection on the leaves was rated after about 14 days. The percent disease control provided by a given test compound was based on the percent disease reduction relative to untreated check plants.

The results are reported in Table 1.

TABLE 1

Preventative Fungicidal Activity (Dosage rate 200) ppm

| COMPOUND NO. | Percent Control | | | | |
|---|---|---|---|---|---|
| | TLB | RB | CLB | BPM | BR |
| 1 | 84 | 0 | 100 | 100 | 92 |
| 2 | 40 | 0 | 85 | 100 | 78 |
| 3 | 0 | 0 | 93 | 100 | 78 |
| 4 | NA | NA | NA | 100 | NA |
| 5 | NA | NA | NA | 100 | NA |
| 6 | NA | NA | 70 | 95 | 46 |
| 7 | 0 | 0 | 59 | 100 | 0 |
| 8 | NA | NA | 96 | 95 | 86 |
| 9 | 84 | NA | 100 | 0 | 100 |
| 10 | 0 | 0 | 100 | 100 | 100 |
| 11 | 85 | 95 | 100 | 100 | 100 |
| 12 | 90 | 86 | 100 | 100 | 100 |
| 13 | 57 | 71 | 100 | 100 | 100 |
| 14 | NA | NA | 100 | NA | 86 |
| 15 | 95 | 100 | 100 | 100 | 100 |
| 16 | 0 | 0 | 100 | 100 | 100 |
| 17 | 95 | 0 | 83 | 100 | 100 |
| 18 | 95 | 0 | 100 | 100 | 100 |
| 19 | 100 | 69 | 100 | 100 | 100 |
| 20 | 95 | 100 | 100 | 100 | 100 |
| 21 | 100 | 0 | 50 | 100 | 100 |
| 22 | 0 | 0 | 41 | 100 | 0 |
| 23 | 0 | 0 | 76 | 100 | 0 |
| 24 | NA | NA | NA | 100 | 86 |

TLB = Tomato Late Blight
RB = Riceblast
CLB = Celery Late Blight
BPM = Bean Powdery Mildew
BR = Bean Rust
NA = Test results not available

What is claimed is:

1. A compound having the formula:

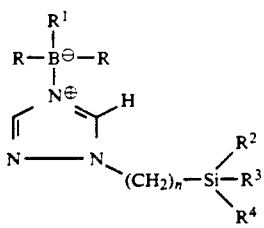

wherein
n is 1 or 2;
R is styryl or the group

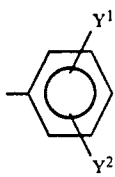

wherein
- Y¹ is hydrogen; lower alkyl having 1 through 6 carbon atoms; fluoro; chloro; lower alkoxy having 1 through 6 carbon atoms, lower alkylthio having 1 through 6 carbon atoms;
- Y² is hydrogen; lower alkyl having 1 through 6 carbon atoms; lower alkylthio having 1 through 6 carbon atoms; or the group

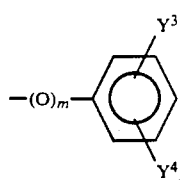

wherein
- m is 0 or 1;
- Y³ and Y⁴ are independently selected from the group of substitutes defined for Y¹;
- R¹ and R⁴ are independently selected from the group of alkyl having 1 through 4 carbon atoms; cycloalkyl having 3 through 6 carbon atoms; lower alkenyl having 2 through 6 carbon atoms; haloalkenyl having 3 through 6 carbon atoms and 1 through 4 halo atoms independently selected from the group of fluoro, chloro, and bromo; or the group

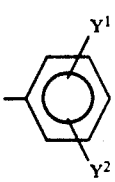

wherein Y¹ and Y² are as hereinabove defined with respect to R;
R² and R³ are independently selected from the group

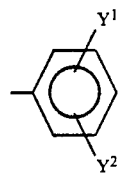

wherein Y¹ and Y² are as defined hereinabove with respect to R.

2. The compound of claim 1 wherein n is 1.
3. The compound of claim 2 wherein R is phenyl.
4. The compound of claim 3 wherein R¹ and R⁴ are either lower alkyl, lower alkenyl, phenyl.
5. The compound of claim 3 wherein R¹ and R⁴ are either methyl, ethyl, vinyl, or phenyl.
6. The compound of claim 3 wherein R² and R³ are the same and are phenyl, 4-halophenyl, or 3-halophenyl.
7. The compound of claim 3 wherein R² and R³ are the same and are 4-fluorophenyl, or 3-fluorophenyl.
8. The compound of claim 3 wherein R² and R³ are the same and are 4-chlorophenyl, or 3-chlorophenyl.
9. The compound of claim 3 wherein R¹ and R⁴ are cycloalkyl having from 3 to 5 carbon atoms.
10. The compound of claim 3 wherein R¹ and R⁴ are cyclopropyl.
11. The compound of claim 3 wherein R is phenyl, R¹ and R⁴ are methyl, vinyl, or phenyl, and R² and R³ are phenyl, 4-halophenyl, or 3-halophenyl.
12. The compound of claim 3 wherein R is phenyl, R¹ and R⁴ are methyl, and R² and R³ are 4-chlorophenyl, or 4-fluorophenyl.
13. The compound of claim 11 wherein said compound is (1-bis(4-chlorophenyl)methylsilylmethyl-1H-,1,2,4-triazole)-diphenylmethylborane.
14. The compound of claim 11 wherein said compound is (1-bis(4-chlorophenyl)methylsilylmethyl-1H-1,2,4-triazole)-triphenylborane.
15. The compound of claim 11 wherein said compound is (1-bis(4-chlorophenyl)methylsilylmethyl-1H-1,2,4-triazole)-diphenylvinylborane.
16. The compound of claim 11 wherein said compound is (1-bis(4-fluorophenyl)methylsilylmethyl-1H-1,2,4-triazole)-diphenylmethylborane.
17. The compound of claim 11 wherein said compound is (1-bis(4-fluorophenyl)methylsilylmethyl-1H-1,2,4-triazole)-triphenylborane.
18. The compound of claim 11 wherein said compound is (1-(bis(4-fluorophenyl)methylsilylmethyl)-1H-1,2,4-triazole)-diphenylvinylborane.
19. A method for controlling fungi which comprises contacting said fungi or its habitats with a fungicidally effective amount of a compound according to claim 1.
20. A method for controlling fungi which comprises contacting said fungi or its habitats with a fungicidally effective amount of a compound according to claim 2.
21. A method for controlling fungi which comprises contacting said fungi or its habitats with a fungicidally effective amount of a compound according to claim 3.
22. A method for controlling fungi which comprises contacting said fungi or its habitat with a fungicidally effective amount of the compound of claim 18.
23. A fungicidal composition comprising a fungicidally effective amount of the compound of claim 1 and a compatible carrier.
24. A fungicidal composition comprising a fungicidally effective amount of the compound of claim 2 and a compatible carrier.
25. A fungicidal composition comprising a fungicidally effective amount of the compound of claim 3 and a compatible carrier.
26. A fungicidal composition comprising a fungicidally effective amount of the compound of claim 18 and a compatible carrier.

* * * * *